United States Patent [19]
Kubota et al.

[11] Patent Number: 5,255,669
[45] Date of Patent: Oct. 26, 1993

[54] ULTRASONIC TREATMENT APPARATUS

[75] Inventors: Tatsuya Kubota, Sagamihara; Kazuya Hijii, Hachioji; Tetsumaru Kubota, Hachioji; Yuichi Ikeda, Hachioji, all of Japan

[73] Assignee: Olympus Optical Co., Ltd., Tokyo, Japan

[21] Appl. No.: 811,881

[22] Filed: Dec. 19, 1991

Related U.S. Application Data

[63] Continuation of Ser. No. 426,887, Oct. 23, 1989, abandoned.

[30] Foreign Application Priority Data

| Apr. 12, 1989 | [JP] | Japan | 1-42014[U] |
| Apr. 27, 1989 | [JP] | Japan | 1-50005[U] |
| Apr. 28, 1989 | [JP] | Japan | 1-51232[U] |
| Jun. 20, 1989 | [JP] | Japan | 1-72179[U] |
| Jun. 20, 1989 | [JP] | Japan | 1-157150 |

[51] Int. Cl.$^5$ .......................... A61H 1/00
[52] U.S. Cl. .................. 128/24 AA; 604/22
[58] Field of Search ........... 128/4, 660.03, 24 AA; 600/167; 606/46, 127, 128; 604/35, 319, 320, 323, 266, 22, 27

[56] References Cited

U.S. PATENT DOCUMENTS

| 3,693,613 | 9/1972 | Kelman | 604/22 |
| 3,802,417 | 4/1974 | Lang | 128/716 |
| 3,805,787 | 4/1974 | Banko . | |
| 3,930,505 | 1/1976 | Wallach | 604/22 |
| 4,024,866 | 5/1977 | Wallach | 604/22 X |
| 4,245,637 | 6/1981 | Nichols | 604/320 |
| 4,425,115 | 1/1984 | Wuchinich | 604/22 |
| 4,431,006 | 1/1982 | Trimmer et al. | 128/24 AA |
| 4,526,571 | 7/1985 | Wuchinich . | |
| 4,670,006 | 6/1987 | Sinnett et al. | 604/35 |
| 4,750,488 | 6/1988 | Wuchinich et al. | 604/22 |
| 4,920,954 | 5/1990 | Alliger et al. | 128/24 AA |
| 4,921,477 | 5/1990 | Davis | 604/22 |

FOREIGN PATENT DOCUMENTS 61-159953 7/1986 Japan .

OTHER PUBLICATIONS

Wells, "Biomedical Ultrasound" Academic Press, 1977, New York, New York.

*Primary Examiner*—William E. Kamm
*Assistant Examiner*—Samuel Gilbert
*Attorney, Agent, or Firm*—Frishauf, Holtz, Goodman & Woodward

[57] ABSTRACT

An ultrasonic treatment apparatus includes an ultrasonic probe having an ultrasonic vibration generator for generating ultrasonic vibrations and a vibration transmission member for transmitting generated vibrations, and a sheath for covering at least an outer peripheral surface of the vibration transmission member of the ultrasonic probe, and a fluid supply unit, attached to an attaching portion of the sheath, for supplying a fluid into a path defined between the vibration transmission member and the sheath. A seal member for sealing the path is arranged nearer to the vibration generator than the attaching portion of the sheath.

7 Claims, 17 Drawing Sheets

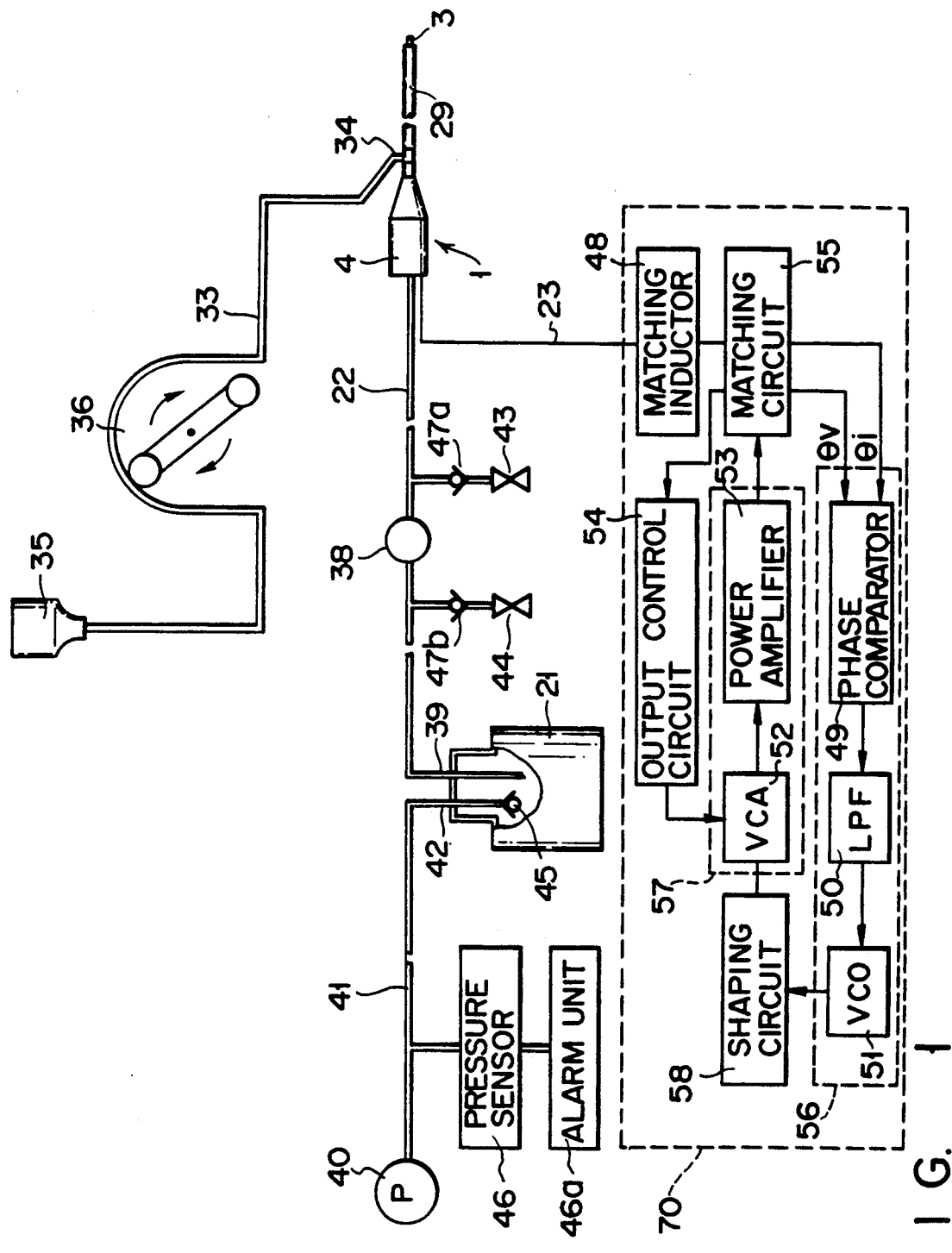
F I G. 1

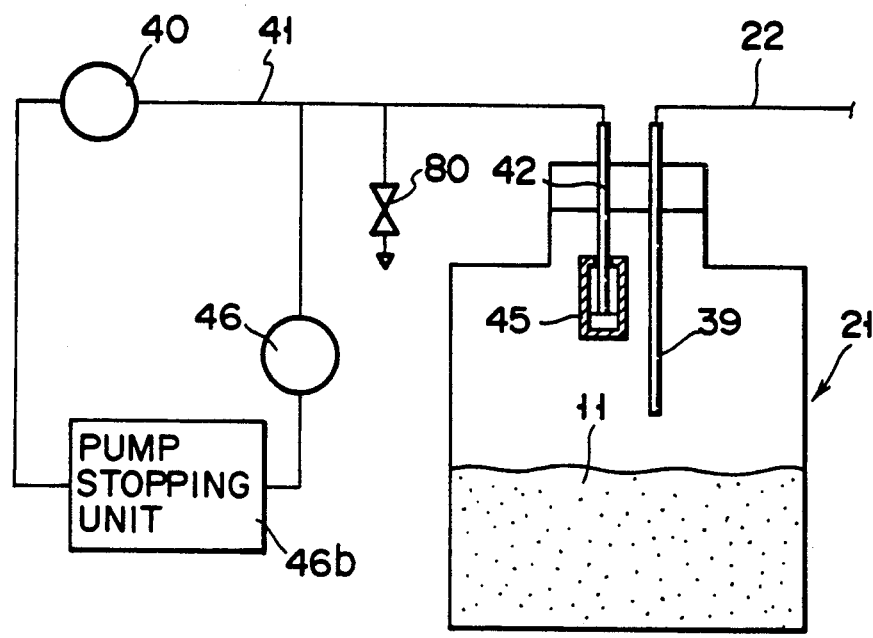
F I G. 7
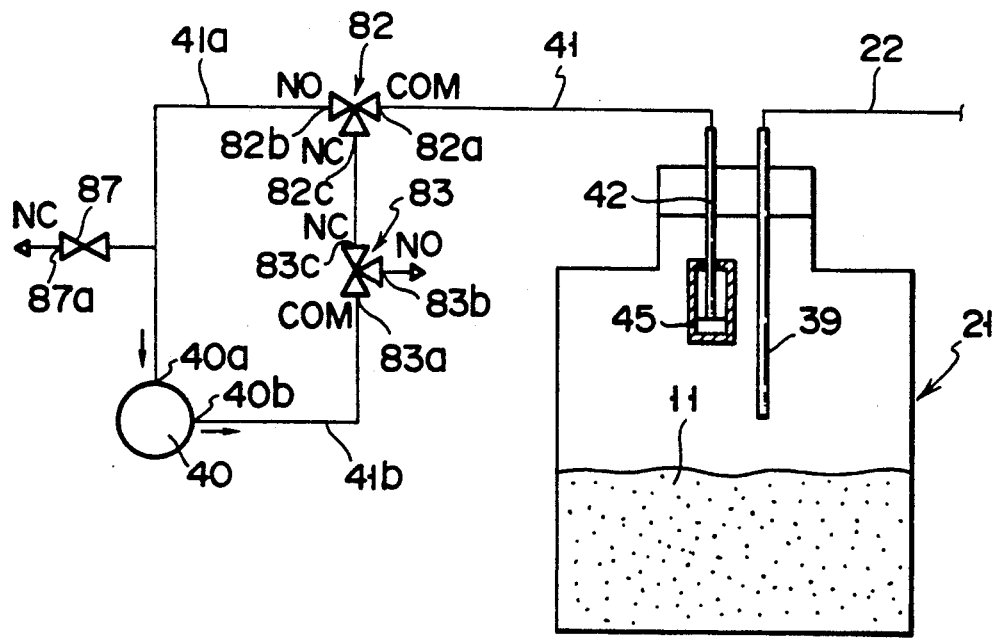
F I G. 8

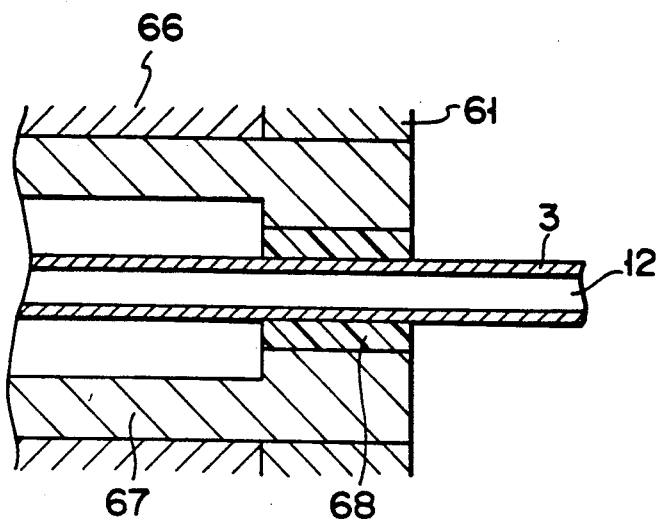
F I G. 10
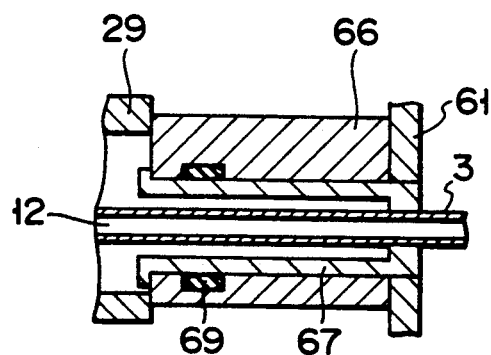
F I G. 11

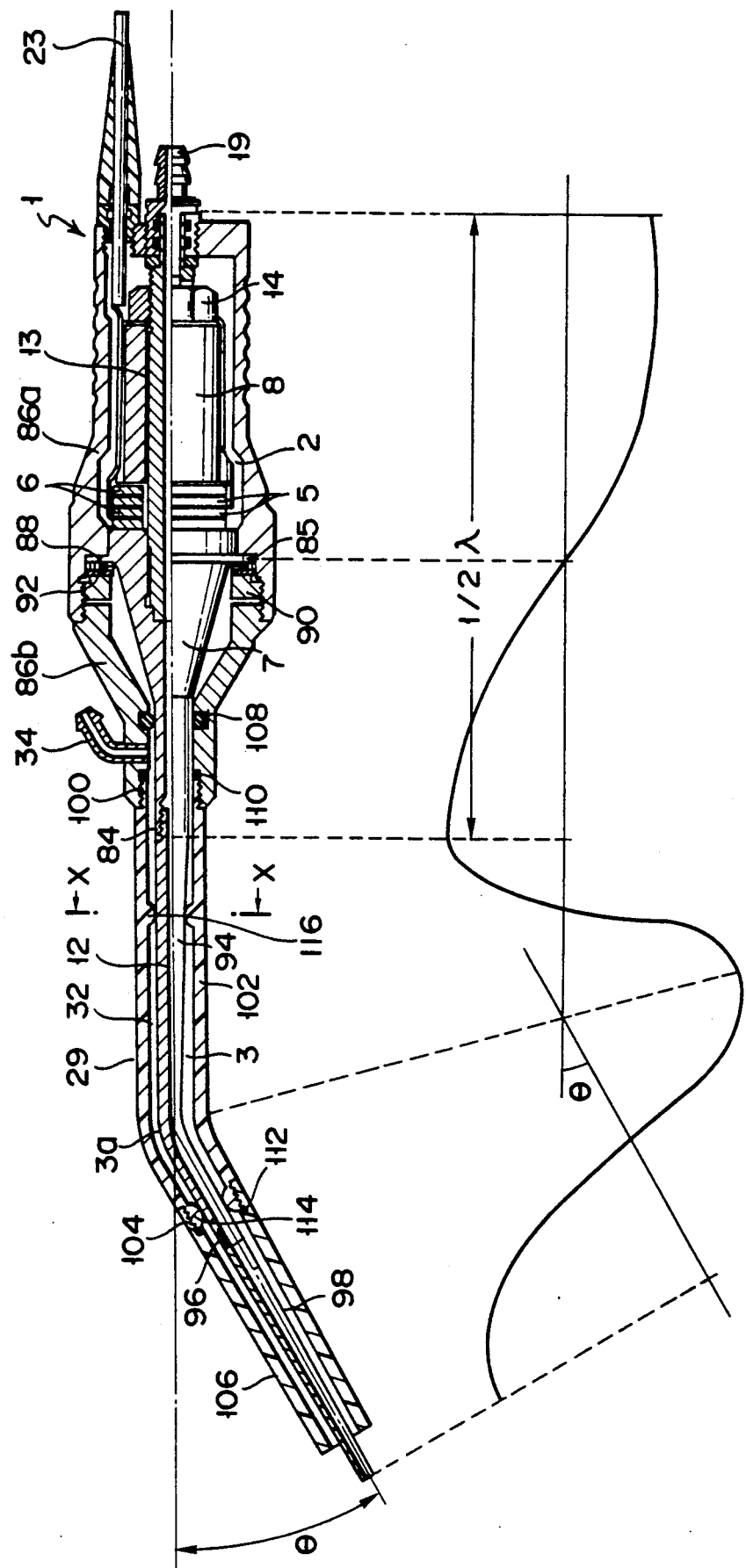
F I G. 17

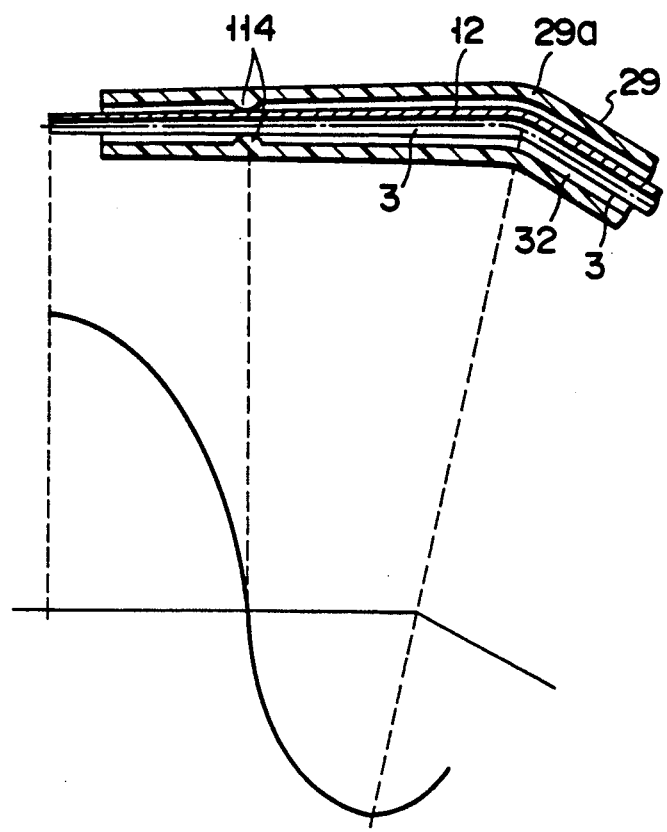
F I G. 20
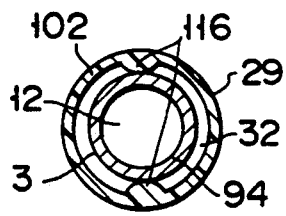
F I G. 18
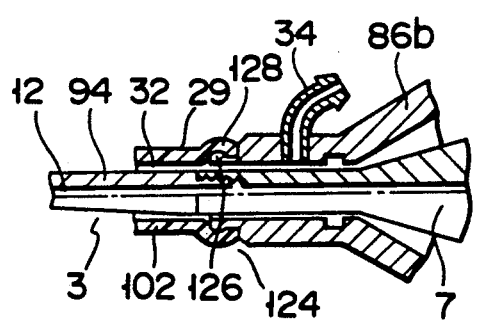
F I G. 21
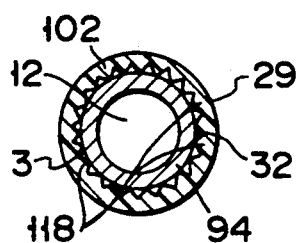
F I G. 19

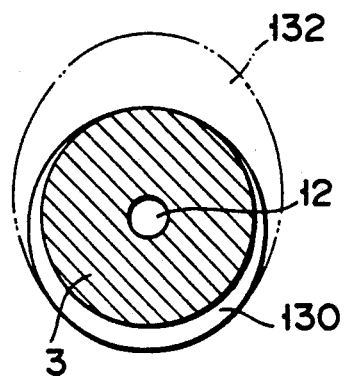
F I G. 28
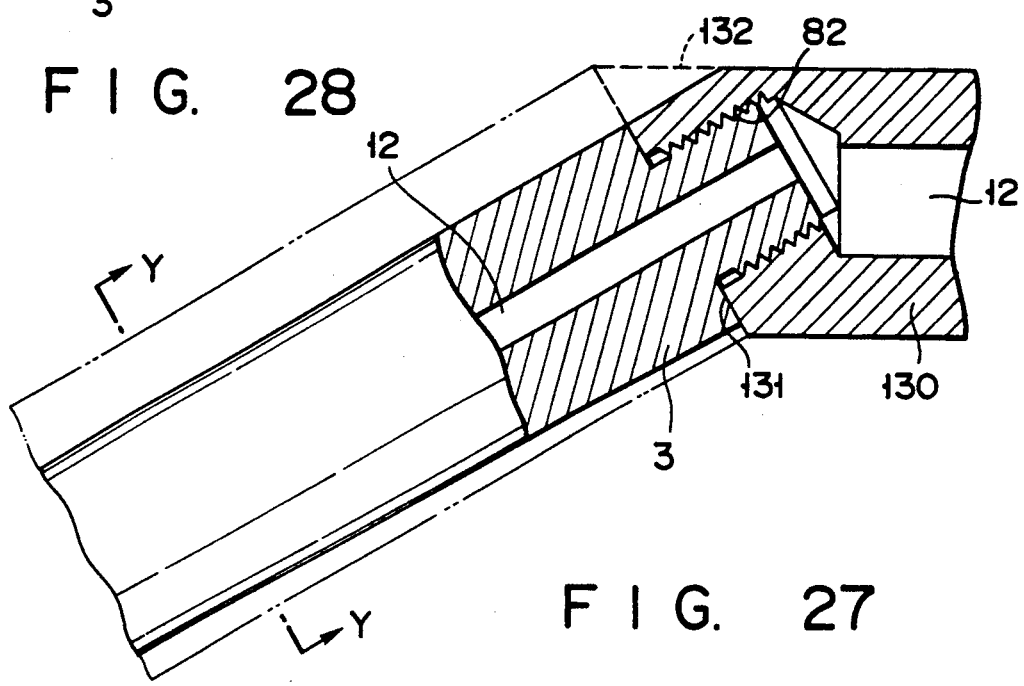
F I G. 27
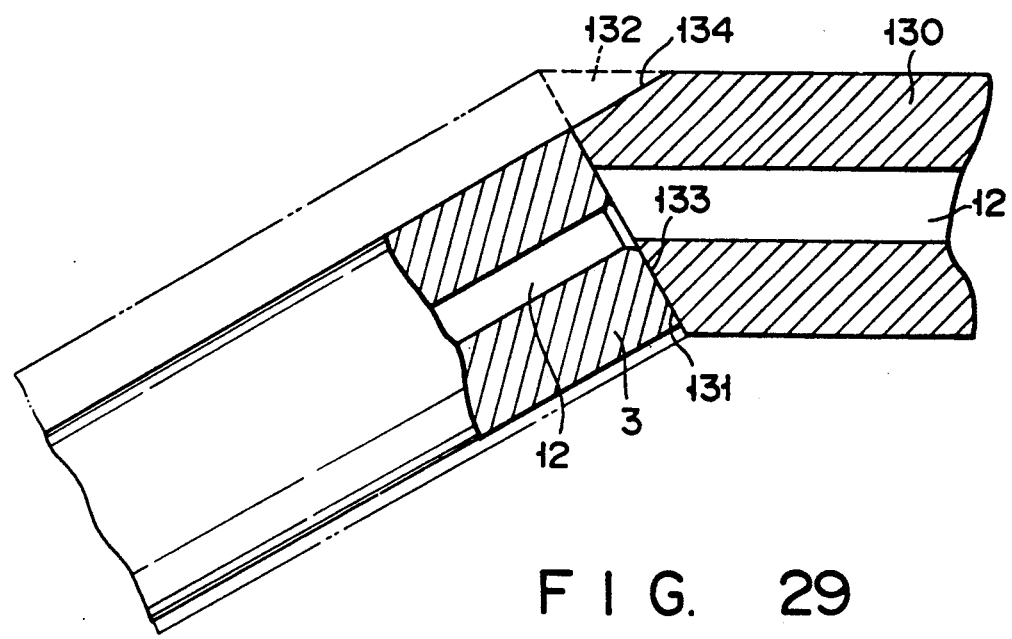
F I G. 29

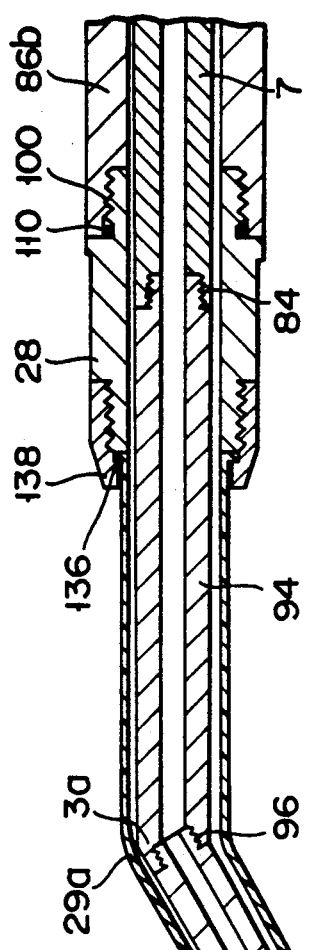
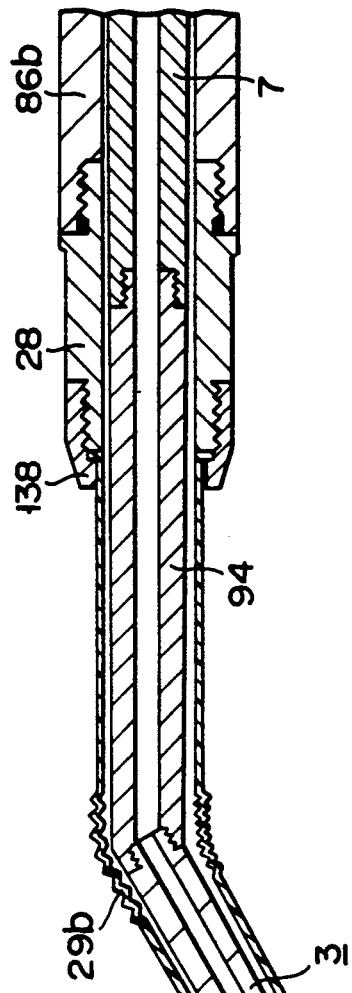

ULTRASONIC TREATMENT APPARATUS

This application is a continuation of application Ser. No. 07/426,887, filed Oct. 23, 1989, now abandoned.

BACKGROUND OF THE INVENTION

1. Field of the Invention
relates to an ultrasonic

The present invention relates to an ultrasonic treatment apparatus which is used in combination with, e.g., an endoscope so as to break a stone in a body or to resect a tissue in a body by emulsifying it.

2. Description of the Related Art

A typical ultrasonic treatment apparatus comprises an ultrasonic oscillator and a vibration transmission member for transmitting ultrasonic vibrations generated by the oscillator to a portion to be treated.

In using this ultrasonic treatment apparatus for a surgical operation, in order to prevent a normal tissue from being adversely affected by heat which is generated by vibrations when the vibration transmission member is brought into contact with a portion other than a morbid portion, or to prevent generation of heat due to vibrations of the vibration transmission member, a technique of covering the vibration transmission member with a sheath and causing a perfusion liquid to flow between the vibration transmission member and the sheath has been proposed. Typical examples of this technique are disclosed in U.S. Pat. Nos. 3,805,787 and 4,425,115.

Published Unexamined Japanese Patent Application No. 61-159953 discloses an ultrasonic treatment apparatus which is used in combination with an endoscope and has a vibration transmission member to be inserted into the channel of the endoscope.

In ultrasonic treatment apparatuses disclosed in U.S. Pat. Nos. 3,805,787 and 4,425,115, a perfusion liquid is supplied to a cover which covers an ultrasonic oscillator and to a portion near the connecting portion of the cover and the sheath. In the ultrasonic treatment apparatus disclosed in Published Unexamined Japanese Patent Application No. 61-159953, when the apparatus is to be used in combination with an endoscope, a portion between the channel of the endoscope and the vibration transmission member is sealed by a rubber plug or the like fitted in the channel opening of the endoscope, and a perfusion liquid is supplied from a portion near the sealed portion into the channel.

SUMMARY OF THE INVENTION

It is an object of the present invention to provide an ultrasonic treatment apparatus which can efficiently dissipate heat generated at a vibration transmission member and can minimize attenuation of vibrations of the vibration transmission member.

In order to achieve the above object, according to the present invention, there is provided an ultrasonic treatment apparatus comprising an ultrasonic probe having ultrasonic vibration generating means for generating ultrasonic vibrations, and a vibration transmission means for transmitting the generated vibrations, a sheath for covering at least an outer peripheral surface of the vibration transmission means of the ultrasonic probe, fluid supply means, attached to an attaching portion of the sheath, for supplying a fluid into a path formed between the vibration transmission means and the sheath, and seal means, arranged at a position closer to the vibration generating means than the attaching portion of the sheath, for sealing the path.

BRIEF DESCRIPTION OF THE DRAWINGS

FIG. 1 is a diagrammatic view showing an arrangement of an ultrasonic treatment apparatus according to the first embodiment of the present invention;

FIG. 7 is a diagrammatic view showing the third modification of the suction system;

FIG. 8 is a diagrammatic view showing the fourth modification of the suction system;

FIGS. 10 and 11 are sectional views showing a seal portion of the ultrasonic treatment apparatus in FIG. 9;

FIG. 17 is a partially cutaway side view of an ultrasonic treatment apparatus according to the sixth embodiment of the present invention;

FIG. 18 is a cross-sectional view taken along a line X—X in FIG. 17;

FIG. 19 is a cross-sectional view showing the first modification of the sheath;

FIG. 20 is a longitudinal sectional view showing the second modification of the sheath;

FIG. 21 is a longitudinal sectional view showing the third modification of the sheath;

FIG. 27 is a partial sectional view showing a vibration transmission member of the ultrasonic treatment apparatus in FIG. 26;

FIG. 28 is a cross-sectional view taken along a line Y—Y in FIG. 27;

FIG. 29 is a partial sectional view showing a modification of the vibration transmission member of the eighth embodiment;

FIG. 30 is a longitudinal sectional view showing an vibration transmission member of an ultrasonic treatment apparatus of the ninth embodiment of the present invention; and FIG. 31 is a longitudinal sectional view showing a modification of a sheath of the ninth embodiment.

DETAILED DESCRIPTION OF THE PREFERRED EMBODIMENTS

Figure 2:
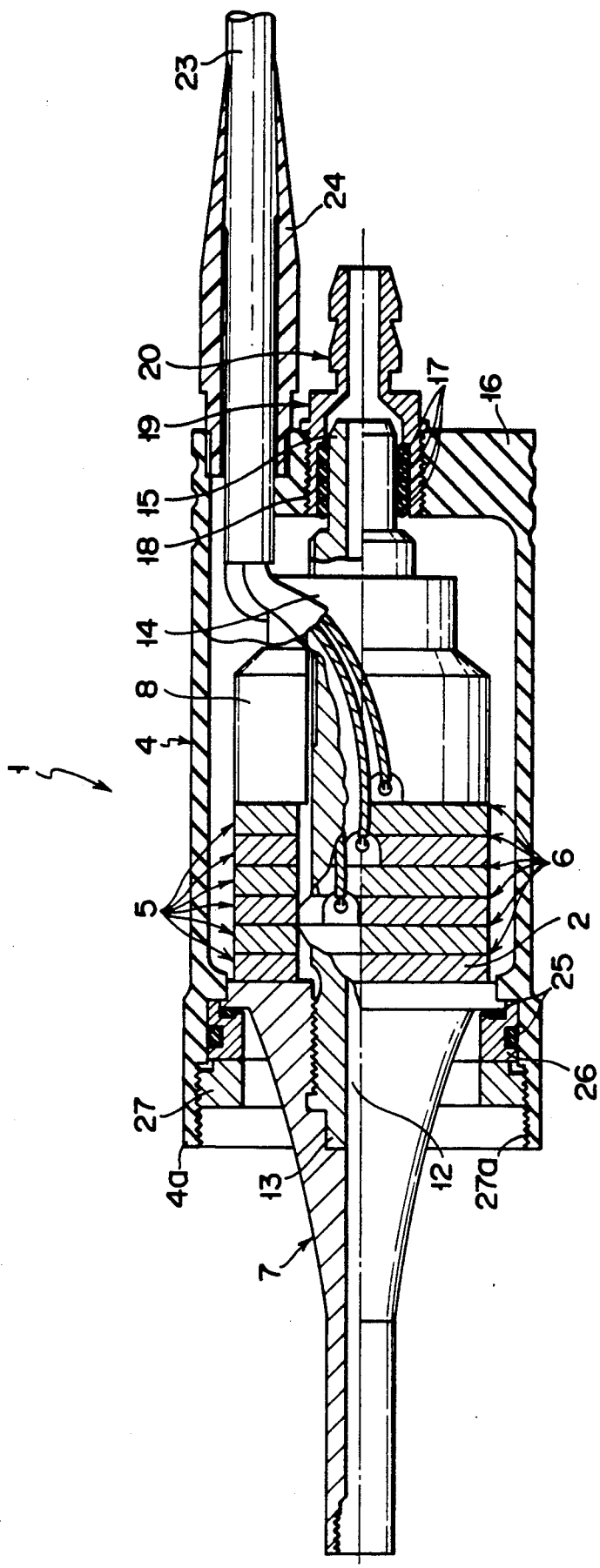
FIG. 2 is a partial sectional view showing a vibration generating section of the ultrasonic treatment apparatus in FIG. 1.
Figure 3:
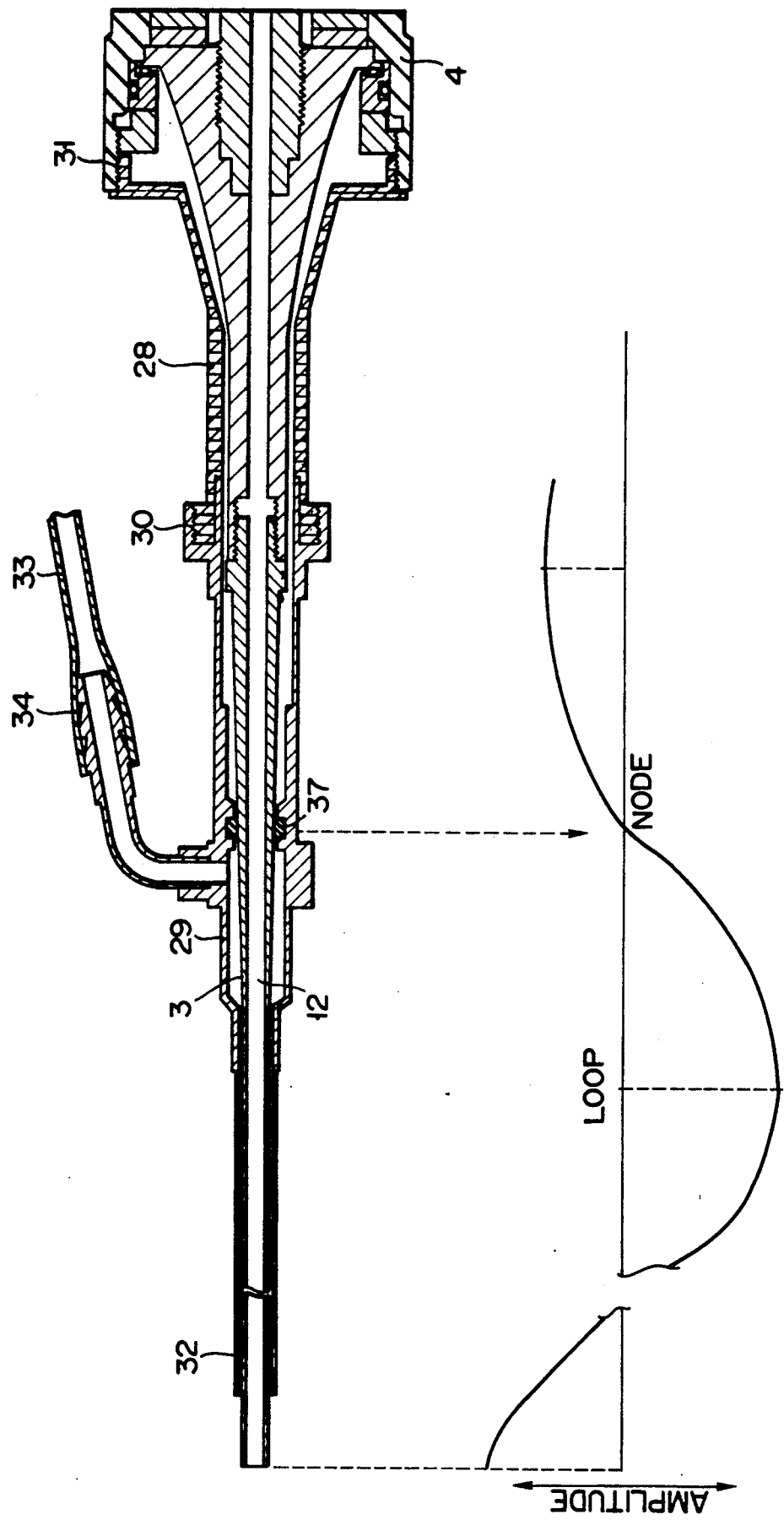
FIG. 3 is a longitudinal sectional view showing a vibration transmission member of the ultrasonic treatment apparatus in FIG. 1.

FIGS. 1 to 3 show the first embodiment of the present invention. FIG. 1 schematically shows a system of an ultrasonic treatment apparatus.

As shown in FIGS. 2 and 3, an ultrasonic probe 1 comprises an ultrasonic oscillator 2 and a vibration transmission member 3. The ultrasonic oscillator 2 is set in a cover 4 as a portion to be gripped. The ultrasonic oscillator 2 is designed such that several piezoelectric elements 5 consisting of, e.g., PZT (Pb-Zirconate-Titanate) and a corresponding number of electrodes 6 are stacked on each other, and the resultant structure is sandwiched between a front metal block (horn) 7 and a rear metal block 8 which have a transformation effect (vibration amplification effect). In addition, a bolt 13 having a suction path 12 extending in its axial direction is inserted in the axial center of the piezoelectric elements 5, the electrodes 6, the front metal block 7, and the rear metal block 8. The distal end of the bolt 13 is threadably engaged with the front metal block 7, and a nut 14 is screwed into the proximal end of the bolt 13. With this arrangement, the piezoelectric elements 5 and the electrodes 6 are tightly clamped between the front and rear metal blocks 7 and 8. Note that the suction path 12 extends through the front metal block 7.

A cylindrical portion 15 is integrally formed with the proximal end of the bolt 13. The proximal end of cylindrical portion 15 protrudes outside through a screw hole 18 formed in a rear wall 16 of the cover 4. A suction piece 19 is screwed/fitted in the screw hole 18. A plurality of O-rings 17 are fitted between the suction piece 19 and the cylindrical portion 15 so as to provide a seal therebetween. A suction tube 22 communicating with a suction vessel 21 is connected to a proximal end portion 20 of the suction piece 19, as shown in FIG. 1.

Referring to FIG. 2, reference numeral 23 denotes a power source cord for applying an RF voltage to the electrodes 6 of the ultrasonic oscillator 2. The power source cord 23 has a bend preventing portion 24 and is attached to the rear wall 16 of the cover 4 by threadable engagement in the same manner as the suction piece 19.

The ultrasonic oscillator 2 having the above-described arrangement is held/fixed in the cover 4 by a fixing member 27 and a seal ring 26 having a plurality of O-rings 25 for holding the cover 4 and the front metal block 7 in a liquid-tight state. A female thread 27a is formed inside a front wall 4a of the cover 4 so as to attach a sheath 29.

More specifically, as shown in FIG. 3, the sheath 29 is attached to the cover 4 through a connecting adapter 28. Threads 30 and 31 are respectively formed on the outer surface of the distal end and the inner surface of the proximal end of the connecting adapter 28. The distal end of the adapter 28 is connected to the sheath 29 by using the thread 30, and the proximal end of the adapter 28 is connected to the front wall 4a of the cover 4 by using the thread 31.

As shown in FIG. 3, the vibration transmission member 3 of the ultrasonic probe 1 is inserted in the sheath 29. A perfusion liquid is supplied into a space 32 between the vibration transmission member 3 and the sheath 29. For this purpose, a mouthpiece 34 to which liquid-supply tube 33 is attached is mounted on an intermediate portion of the sheath 29. One end of the tube 33 is connected to the mouthpiece 34.

As shown in FIG. 1, the other end of the liquid-supply tube 33 is connected to a liquid-supply bottle 35. The bottle 35 stores a physiological saline solution or the like. A roller pump 36 as a means for pouring a perfusion liquid is arranged midway along the liquid-supply tube 33 between the liquid-supply bottle 35 and the mouthpiece 34. The perfusion liquid pouring means is not limited to the roller pump 36 but various methods of pouring a perfusion liquid can be used, e.g., a method of utilizing gravitational falling and a method of using a bimorph pump.

An O-ring, that is, a seal member 37 for providing a seal between the inner surface of the sheath 29 and the outer surface of the vibration transmission member 3 is arranged inside an intermediate portion of the sheath 29 which covers the vibration transmission member 3. The seal member 37 is located closer to the proximal end than the mounting position of the mouthpiece 34 to which the liquid-supply tube 33 is attached. The seal member 37 prevents a perfusion liquid, supplied from the liquid-supply bottle 35 through the mouthpiece 34, from flowing rearward.

As shown in FIG. 3, the mounting position of the seal member 37 coincides with the position of a node of ultrasonic vibrations of the vibration transmission member 3, or may not perfectly coincide therewith as long as it is located near the node.

As shown in FIG. 1, an opening/closing valve 38 is arranged in the suction tube 22 for connecting the ultrasonic probe 1 to the suction vessel 21 so as to block a liquid flow in the suction tube 22 when a suction operation is stopped. In addition, an ultrasonic probe side mouthpiece 39 and a pump side mouthpiece 42 are mounted on the opening of the suction vessel 21 so as to remove stones and tissues, which are broken and resected by the ultrasonic probe 1, together with a perfusion liquid through the suction tube 22. An exhaust tube 41 whose end is connected to a suction pump 40 is connected to the mouthpiece 42 so as to evacuate the suction vessel 21 to a negative pressure.

A solenoid valve 43 is arranged midway along the suction tube 22 between the opening/closing valve 38 and the ultrasonic probe 1. When a suction operation is stopped, the solenoid valve 43 is opened to release the pressure in the path extending through the vibration transmission member 3 to the atmosphere.

Similarly, a solenoid valve 44 is arranged midway along the suction tube 22 between the opening/closing valve 38 and the suction vessel 21. When a suction operation is stopped, the solenoid valve 44 is opened to hold the negative pressure in the suction vessel 21 at a predetermined value.

Check valves 47a and 47b are respectively arranged in the tubes extending from the solenoid valves 43 and 44 so as to prevent a waste liquid or humid air from flowing therein.

A float type check valve 45 is arranged at the pump-side mouthpiece 42 of the suction vessel 21. When the level of a waste liquid reaches a predetermined value, the check valve 45 is closed to prevent the waste liquid from flowing from the mouthpiece 42 to the suction pump 40.

A pressure sensor 46 is arranged midway along the exhaust tube 41 between the suction vessel 21 and the suction pump 40. A detection signal from the pressure sensor 46 is supplied to an alarm unit 46a for generating an alarm when the suction force exceeds a predetermined value.

The power source cord 23 for applying an RF voltage to the electrodes 6 of the ultrasonic oscillator 2 is connected to a driver 70 shown in FIG. 1. An arrangement of the driver 70 will be described below. Reference numeral 48 denotes a matching inductor for correcting the phase of the ultrasonic oscillator 2. The matching inductor 48 is connected to a resonance frequency tracking phase-locked loop (PLL) 56 through a matching circuit 55. The phase-locked loop 56 is constituted by a phase comparator 49, a low-pass filter 50, and a voltage-controlled oscillator 51 so as to be driven at a plurality of resonance frequencies of the ultrasonic oscillator 2. The phase comparator 49 detects a voltage-current phase difference of the ultrasonic oscillator 2. The low-pass filter (LPF) 50 integrates a detection signal from the phase comparator 49 and outputs a DC control voltage to the voltage-controlled oscillator (VCO) 51. The oscillation frequency of the voltage-controlled oscillator 51 is changed by the control voltage. Reference numeral 52 denotes a voltage-controlled amplifier (VCA) for controlling the amplitude of the ultrasonic oscillator 2 to be constant; and 53, a power amplifier for amplifying an output signal from the voltage-controlled amplifier 52 to a power enough to drive the ultrasonic oscillator 2. The voltage-controlled amplifier 52 and the power amplifier 53 constitute a driving circuit 57.

Reference numeral 54 denotes an output control circuit for controlling the voltage-controlled amplifier 52 to cause the oscillator 2 to perform a constant-amplitude operation. The matching circuit 55 includes a circuit for efficiently transferring a driving output from the power amplifier 53 to the vibration system, and a circuit for extracting a value and signals representing the magnitude of the output, e.g., a current value and voltage and current phase signals.

Reference numeral 58 denotes a shaping circuit for shaping a distorted output waveform from the voltage-controlled oscillator (VCO) 51.

With this arrangement, an output from the voltage-controlled oscillator (VCO) 51 is corrected by the shaping circuit 58 and is applied to ultrasonic oscillator 2 through the voltage-controlled amplifier (VCA) 52, the power amplifier 53, and the matching circuit 55. As a result, the electric energy is converted into vibration energy.

The voltage-controlled amplifier (VCA) 5 keeps the driving current constant so as to hold the amplitude of ultrasonic vibrations of the ultrasonic probe 1 constant. In addition, the voltage-controlled amplifier 52 is feedback-controlled by an output from the matching circuit 55 through the output control circuit 54. The power amplifier 53 amplifies an output signal from the voltage-controlled amplifier 52 to a power enough to drive the ultrasonic probe 1.

The matching circuit 55 includes an impedance matching circuit for efficiently transferring an output from the power amplifier 53 to the ultrasonic oscillator 2, and a circuit for extracting a value and signals representing the magnitude of the output, e.g., a current value $i$ and voltage and current phase signals $\theta v$ and $\theta i$. The current value i is supplied to the voltage-controlled amplifier 52 through the output control circuit 54.

The phase correcting inductor 48 is connected to the ultrasonic oscillator 2 so as to cancel a damping capacity Cb of the ultrasonic oscillator 2.

The voltage and current phase signals $\theta v$ and $\theta i$ corresponding to a resonance frequency fr of the ultrasonic probe 1 and extracted from the matching circuit 55 are supplied to the phase-locked loop 56. Consequently, the ultrasonic probe 1 is driven at the resonance frequency fr.

In the ultrasonic probe 1 which is driven in this manner, electric energy is converted into vibration energy, and ultrasonic vibrations are transmitted to the tip of the vibration transmission member 3. For example, the tip of the vibration transmission member 3 is urged against a stone to break it or against a tissue to emulsify/resect it.

Meanwhile, a perfusion liquid is poured from the liquid-supply bottle 35 into the space 32 in the sheath 29 through the liquid-supply tube 33 by using the roller pump 36, thereby cooling the vibration transmission member 3, or cleaning a morbid portion by injecting the perfusion liquid from the tip of the member 3. Since the rear region of the space 32 in the sheath 29 is sealed by the seal member 37, the perfusion liquid does not flow toward the proximal end portion of the ultrasonic probe 1.

As is apparent from a vibration distribution shown in FIG. 3, the seal member 37 is arranged in contact with the outer surface of the vibration transmission member 3 at a node of vibrations of the vibration transmission member 3. Since the seal member 37 is located at the node where only little vibration occurs, attenuation of a vibration amplitude can be minimized. With the ultrasonic treatment apparatus having the above-described arrangement, an efficient, quick treatment can always be performed.

When the ultrasonic treatment apparatus is operated, the suction vessel 21 is evacuated by the suction pump 40 through the exhaust tube 41 so as to remove broken stones or emulsified/resected tissues by drawing them through the suction path 12 and the suction tube 22.

While the apparatus is not operated, the opening/closing valve 38 disconnects the path between the ultrasonic probe 1 and the suction vessel 21, and the suction path 12 in the vibration transmission member 3 is sealed with its negative pressure remaining. If the solenoid valve 43 is released to the atmosphere for a predetermined period of time, the negative pressure in the suction path 12 is released, and hence suction of the tip of the vibration transmission member 3 to a stone or a tissue can be released.

In this case, the check valve 47a prevents a waste liquid or humid air from flowing into the solenoid valve 43.

The solenoid valve 44 serves to adjust the pressure in the suction vessel 21 to a predetermined internal pressure when the opening/closing valve 38 is released during a suction operation. Therefore, a suction operation can be started at the same time when the opening/closing valve 38 is released to start an operation. In this case, the check valve 47b has the same function as that of the check valve 47a.

If the suction path 12 or the suction tube 22 clogs up during a suction operation, or the pressure in the tube/path exceeds a predetermined value, the alarm unit 46a is operated to generate an alarm in response to a detection signal from the pressure sensor 46.

If a predetermined amount of waste liquid is stored in the suction vessel 21 and the liquid level rises, the float type check valve 45 is vertically raised to block the flow path. Hence, no waste liquid flows into the suction pump 40. In this case, the pressure in the exhaust tube 41 connected to the suction pump 40 is increased, and the pressure sensor 46 performs the same operation as described above.

A suction system arranged in the ultrasonic treatment apparatus of the present invention will be described below in detail.

Figure 4:
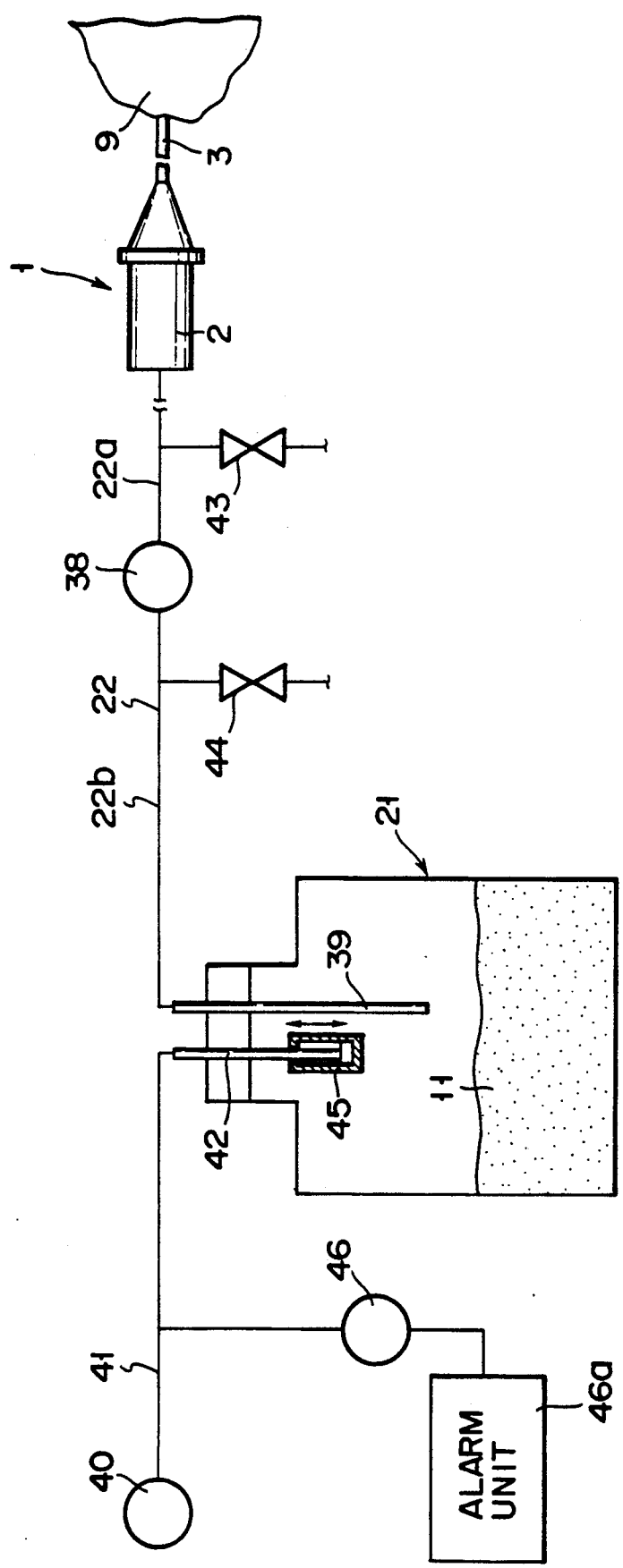
FIG. 4 is a diagrammatic view showing a suction system of the ultrasonic treatment apparatus in FIG. 1.

Referring to FIG. 4, reference numeral 21 denotes a suction storage vessel constituted by a closed suction bottle for storing a suction sample 11 extracted from a morbid portion in a body cavity. In the suction storage vessel 21, a sample introducing pipe, i.e., a probe-side mouthpiece 39, to which a suction tube 22 is connected, vertically extends downward, and a pump-side mouthpiece 42, to which an exhaust tube 41 is connected, vertically extends downward. The lower end opening of the pump-side mouthpiece 42 is located above the lower end opening of the probe-side mouthpiece 39. The suction pump 40 serves as a suction source for evacuating the suction storage vessel 21 to a negative pressure. A pressure sensor 46 is connected to the exhaust tube 41 between the suction pump 40 and the vessel 21. The pressure sensor 46 detects an abnormal negative pressure when the suction tube 22 clogs up and an excess negative pressure is set in the vessel 21. An alarm unit 46a is electrically connected to the pressure sensor 46. The alarm unit 46a serves as an abnormality response means which is operated in response to a sensor signal, which is output when the pressure sensor 46 detects an abnormal negative pressure, so as to inform an operator of an abnormal state with an alarm sound or an alarm indicator lamp.

An opening/closing valve 38 is arranged midway along the suction tube 22 so as to block a suction flow in the suction tube 22 when the operation of the ultrasonic probe 1 is stopped. A first solenoid 43 is arranged midway along a suction path 22a between the opening/closing valve 38 and an ultrasonic oscillator unit 2. When the operation of the ultrasonic probe 1 is stopped, the solenoid valve 43 is opened to release the pressure in the suction path 22a to the atmosphere. A second solenoid valve 44 is arranged midway along a suction path 22b between the opening/closing valve 38 and the suction storage vessel 21. When the operation of the ultrasonic probe 1 is stopped, the solenoid valve 44 is opened to release the pressure in the suction path 22b to the atmosphere. In addition, a normally-open check valve 45 is arranged at the exhaust port of the pump-side mouthpiece 42. When a suction sample 11 in the suction storage vessel 21 exceeds a predetermined storage amount, the check valve 45 is raised with an increase in liquid level of the sample 11 so as to automatically close the exhaust port of the mouthpiece 42.

In this suction system, if the suction tube 22 clogs up and the pressure in the vessel 21 is lowered below a predetermined negative pressure, i.e., becomes an excess negative pressure (abnormal negative pressure) during a suction operation, the pressure sensor 46 detects an abnormal state of this excess negative pressure. In response to a signal from the pressure sensor 46, the alarm unit 46a as an abnormality response means is operated to inform an operator of the abnormal state due to the suction path clogging with an alarm sound or the like. Therefore, if the operator stops the use of the apparatus immediately after knowing the abnormal state, heating of the oscillator or the vibration transmission member 3 of the ultrasonic probe 1, breakage thereof, and the like can be prevented.

In addition, if a suction sample 11 is stored in the suction storage vessel 21 and the liquid level exceeds a predetermined level, the check valve 45 is vertically raised with an increase in liquid level of the sample 11 so as to automatically close the exhaust port of the pump-side mouthpiece 42. With this arrangement, there is no possibility that the sample 11 flows into the suction pump 40 and the pressure sensor 46, and hence the service lives of the suction pump 40 and the pressure sensor 46 can be prolonged. Moreover, since an excess negative pressure is set in the exhaust tube 41 upon closing of the check valve 45, the pressure sensor 46 is operated in the same manner as in the case wherein the suction tube 22 clogs up. As a result, the alarm unit 46a is operated to inform an operator of an abnormal state with an alarm sound or the like when the vessel is filled up with the sample 11.

Figure 5:
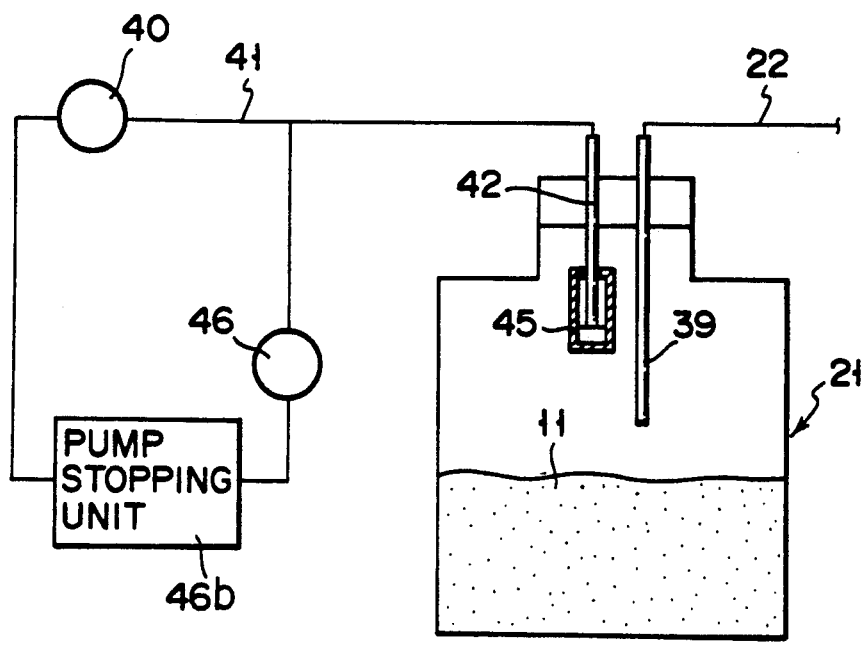
FIG. 5 is a diagrammatic view showing the first modification of the suction system.

In the first embodiment, the alarm unit 46a is used as a means for informing an abnormal state of the suction system. However, a pump stopping unit 46b connected to the suction pump 40 as shown in FIG. 5 may be used in place of the alarm unit 46a of the first embodiment. In this first modification, when the pressure sensor 46 detects an abnormal negative pressure, the pump stopping unit 46b is operated to automatically stop the suction pump 40. With this arrangement, an abnormal state due to tube clogging or filling up of the vessel can be informed to an operator by stopping the pump. In addition, since no excess load is applied to the pump 40, its service life can be prolonged.

Figure 6:
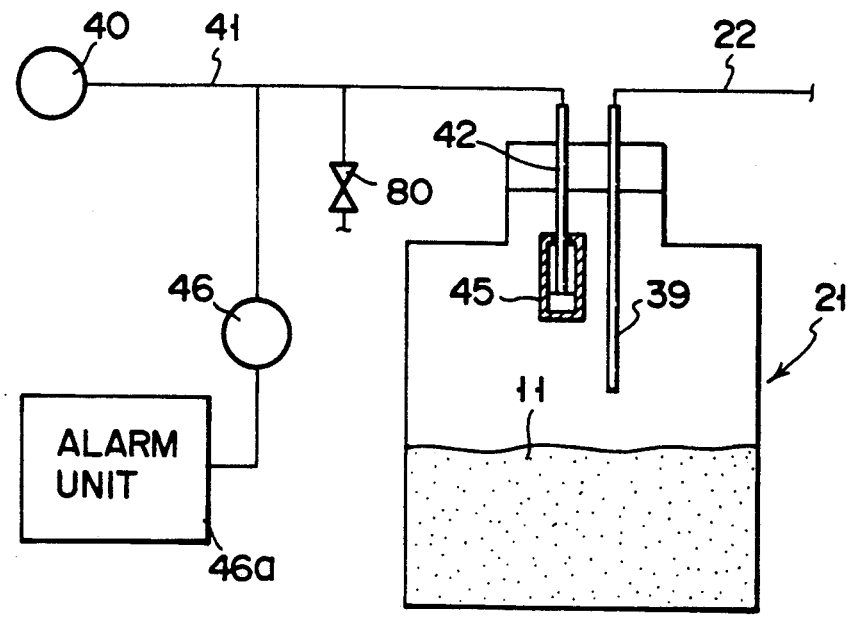
FIG. 6 is a diagrammatic view showing the second modification of the suction system.

FIG. 6 shows the second modification of the suction system. In the second modification, a third solenoid valve 80 is arranged between the check valve 45 and the pressure sensor 46. The solenoid valve 80 is opened at the start of a pump operation so as to release the pressure in the exhaust tube 41 to the atmosphere, and is automatically closed after a predetermined period of time. In this case, when the check valve 45 closes the exhaust port of the pump-side mouthpiece 42, even if the operation is temporarily stopped to remove the suction sample 11 in the suction storage vessel 21, the negative pressure in the exhaust tube 41 is kept. Therefore, the check valve 45 keeps closing the exhaust port of the pump-side mouthpiece 42.

When the pump 40 is to be started again, the third solenoid valve 80 is kept open for a predetermined period of time so as to release the pressure in the exhaust tube 41 to the atmosphere. As a result, the check valve 45 moves downward by its own weight to be opened. Therefore, if the vessel 21 is filled up with the suction sample 11, a state of a normal suction operation can be restored by simply removing the sample 11 stored in the vessel 21 and starting the pump 40. Note that the third solenoid valve 80 may be arranged midway along the tube between the check valve 45 and the pressure sensor 46 of the first modification shown in FIG. 5 so as to constitute a system shown in FIG. 7.

FIG. 8 shows the fourth modification of the suction system. In the fourth modification, a suction path extends from the tip of the vibration transmission member 3 to the pump 40 through the suction tube 22 and a suction vessel 21. A first three-way solenoid valve 82 is arranged in the exhaust tube 41 between the suction vessel 21 and the pump 40. In the first solenoid valve 82, a common (COM) port 82a is connected to the pump-side mouthpiece 42 through the exhaust tube 41; a normally-open (NO) port 82b, to a pump inlet port 40a through the exhaust tube 41a; and a normally-closed (NC) port 82c, to a pump outlet port 40b through a second three-way solenoid valve 83. In the second solenoid valve 83, an NC port 83c is connected to the NC port 82c of the first solenoid valve 82, an NO port 83b communicates with the atmosphere, and a COM port 83a is connected to the pump outlet port 40b. A two-way solenoid valve 87 is arranged in a branch path formed midway along the exhaust tube 41a between the NO port 82b of the first solenoid valve 82 and the pump inlet port 40a. An NC port 87a of the two-way solenoid valve 87 communicates with the atmosphere.

In the suction system according to the fourth modification, the COM port 82a and the NO port 82b of the first solenoid valve 82 communicate with each other during a suction operation, a resected tissue or a piece of flesh is drawn through the tip of the vibration transmission member 3. In this case, the COM port 83a and the NO port 83b of the second solenoid valve 83 communicate with each other, and hence the compressed air is released to the atmosphere.

If the suction path clogs up and a suction operation is stopped, the first and second solenoid valves 82 and 83 are simultaneously excited. As a result, the COM ports 82a and 83a and the NC ports 82c and 83c of the respective solenoid valves communicate with each other. In addition, the solenoid valve 87 is excited simultaneously with the solenoid valves 82 and 83 so as to cause the pump inlet port 40a to communicate with the atmosphere. As a result, the compressed air discharged from the pump outlet port 40b is supplied to the tip of the vibration transmission member 3 through the NC ports 83c and 82c and the COM port 82a. Note that the first and second solenoid valves 82 and 83 are simultaneously excited for a predetermined period of time after the suction operation is stopped. Hence, the non-excited state of the solenoid valves 82 and 83 is restored after a lapse of the predetermined period of time.

As described above, in the suction system according to the fourth modification, by switching the flow paths of compressed air from the pump 40 and applying a pressure in the suction path, the tissue or the like adhering to the tip of the vibration transmission member 3 can be blown off to eliminate a clogging state of the suction path.

Figure 9:
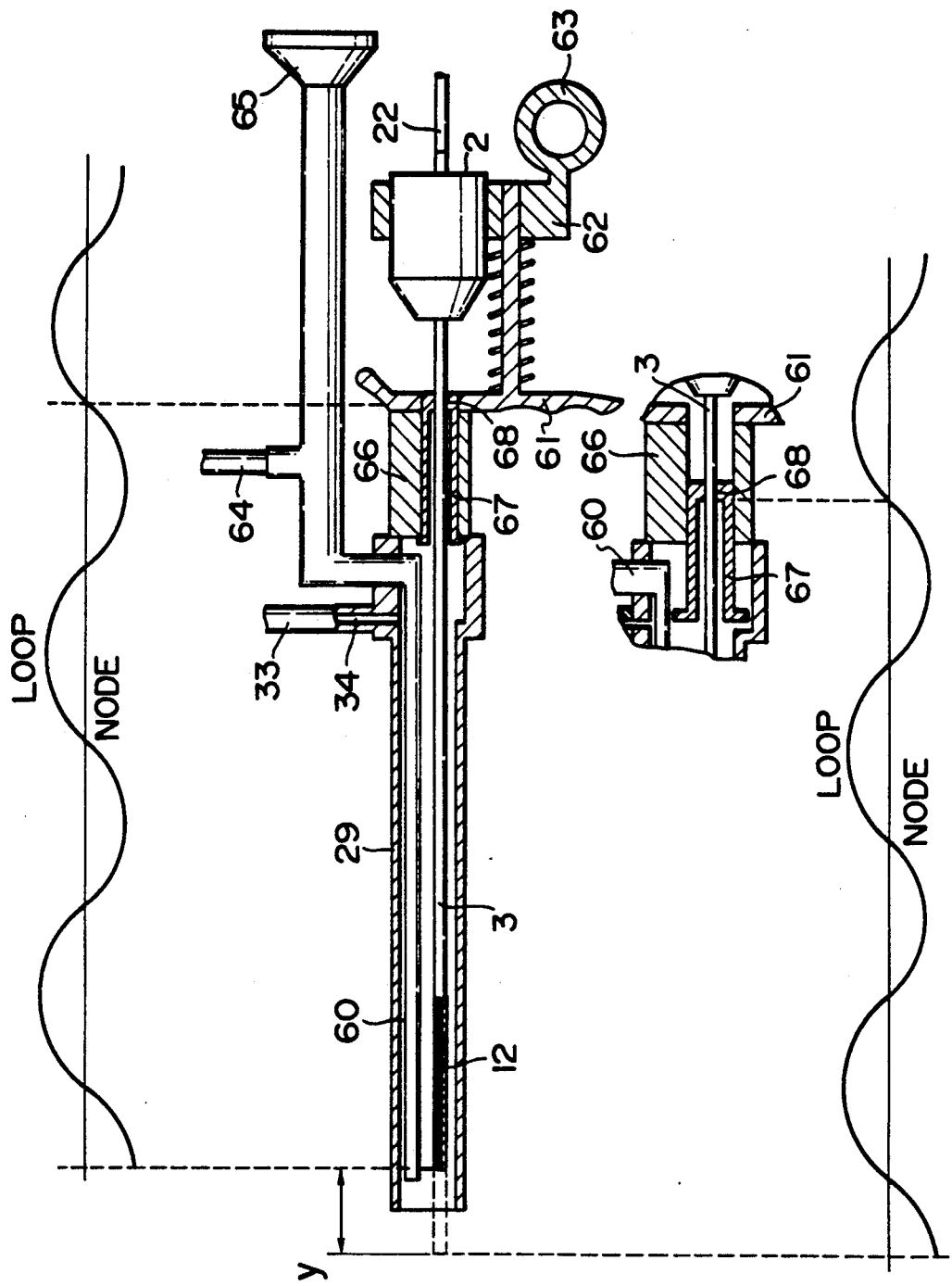
FIG. 9 is a partially cutaway side view of an ultrasonic treatment apparatus according to the second embodiment of the present invention.

FIGS. 9 to 11 show an ultrasonic treatment apparatus according to the second embodiment of the present invention. The ultrasonic treatment apparatus of the second embodiment comprises a tubular sheath 29, a vibration transmission member 3 inserted in the sheath 29, and a scope (fiber scope) 60. A liquid-supply mouthpiece 34 to which a liquid-supply tube 33 is connected is arranged at the proximal end of the sheath 29. A perfusion liquid can be supplied from the mouthpiece 34 into the sheath 29 through the liquid-supply tube 33.

In addition, a grip operation portion 61 for moving the vibration transmission member 3 back and forth is formed at the proximal end of the sheath 29. The grip operation portion 61 includes a slider 62 to which an ultrasonic oscillator unit 2 is attached. By sliding the slider 62 in the distal end direction of the sheath 29, the vibration transmission member 3 can be caused to protrude from the distal end opening of the sheath 29. Note that a ring 63 on which the thumb of an operator is hooked is attached to the slider 62.

A suction path 12 for drawing resected tissues is formed in the vibration transmission member 3. The suction path 12 communicates with a suction tube 22 connected to the proximal end of the ultrasonic oscillator unit 2. A suction pump 40 is connected to the suction tube 22. Referring to FIG. 9, reference numeral 64 denotes a light guide; and 65, an eyepiece portion of the scope.

The grip operation portion 61 is attached to a sheath fixing member 66. A slide member 67 is mounted in an inner hole portion formed in the grip operation portion 61 and the sheath fixing member 66. As indicated by a lower portion in FIG. 4, the slide member 67 is arranged to be slidable in the axial direction. The slide member 67 is liquid-tightly attached to the sheath fixing member 66. In addition, as shown in FIG. 10, a seal portion 68 for liquid-tightly sealing/fixing the vibration transmission member 3 is arranged in the slide member 67. In the second embodiment, the seal portion 68 consists of a Teflon member which is highly resistant to heat generated by vibrations and is forcibly inserted/-fixed between the slide member 67 and the vibration transmission member 3.

As is apparent from the correspondence between the vibration transmission member 3 and a vibration distribution shown in FIG. 9, the seal portion 68 is located at the position of a node of vibrations. In order to provide a seal between the sheath fixing member 66 and the slide member 67, liquid-tight fitting may be performed as shown in FIG. 10, or an O-ring 69 or the like may be used as shown in FIG. 11.

When a tissue is to be removed by using the ultrasonic treatment apparatus, the vibration transmission member 3 is inserted in the sheath 29, and the tip of the sheath 29 is set near the tissue.

Subsequently, the grip operation portion 63 is operated to cause the vibration transmission member 3 to protrude from the sheath 29, and the tip of the member 3 is urged against the morbid tissue. If the ultrasonic oscillator 2 is driven by the above-described driver 70 in this state, a treatment of resecting/emulsifying the tissue can be performed with the tip of vibration transmission member 3.

As described above, in the ultrasonic treatment apparatus having the above-described arrangement, since the seal portion 68 of the vibration transmission member 3 always coincides with a node of vibrations even at the operation start time and at the time when the probe is slid forward, no attenuation of vibrations occur at the seal portion 68. Therefore, a treatment of, e.g., resecting/emulsifying a tissue can be efficiently, reliably, and quickly performed.

Figure 12:
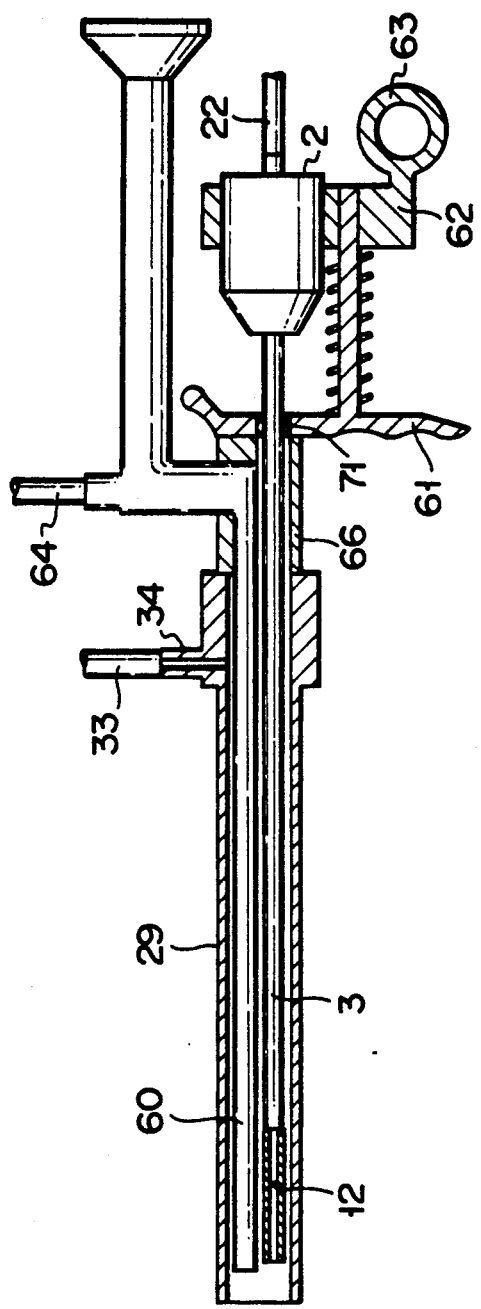
FIG. 12 is a partially cutaway side view of an ultrasonic treatment apparatus according to the third embodiment of the present invention.

FIG. 12 shows the third embodiment of the present invention. In the third embodiment, a seal member 71 has the functions of both the slide member 67 and the seal member in the second embodiment. The seal member 71 is fixed to a portion of a vibration transmission member 3 which corresponds to a node of vibrations. The seal member 71 is designed to be in slidable contact with the circumferential surface of a communicating hole formed in a grip operation portion 61 and a sheath fixing member 66. Other arrangements in the third embodiment are the same as those in the second embodiment.

Figure 13:
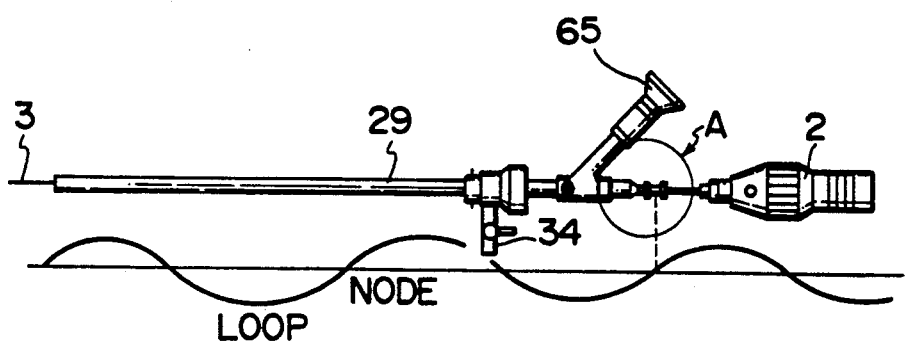
FIG. 13 is a side view of an ultrasonic treatment apparatus according to the fourth embodiment of the present invention.
Figure 14:
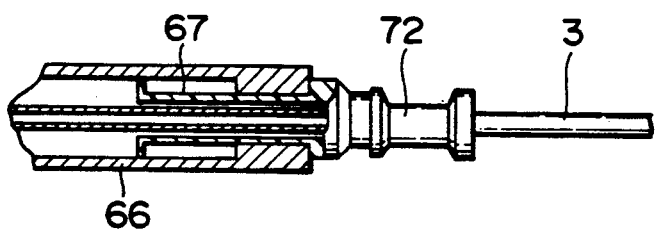
FIG. 14 is a partial sectional view showing a seal portion of the ultrasonic treatment apparatus in FIG. 13.

FIGS. 13 and 14 show the fourth embodiment of the present invention. In the fourth embodiment, a seal member 72 and a slide member 67 are independently formed. A rubber cap or the like may be used as the seal member 72.

Figure 15:
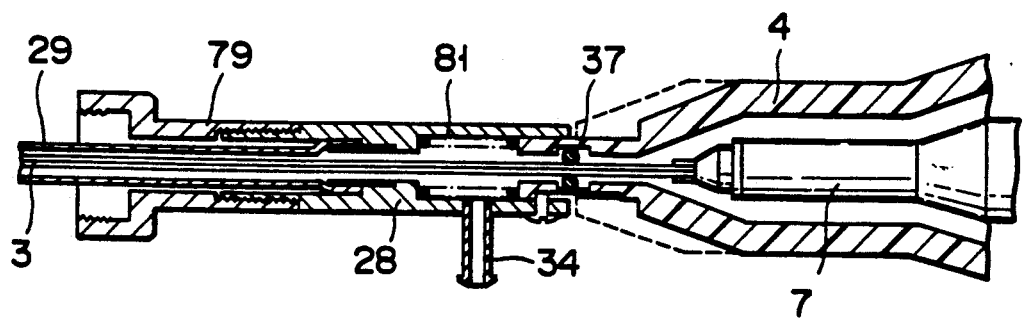
FIG. 15 is a longitudinal sectional view showing a seal portion of an ultrasonic treatment apparatus according to the fifth embodiment of the present invention.
Figure 16:
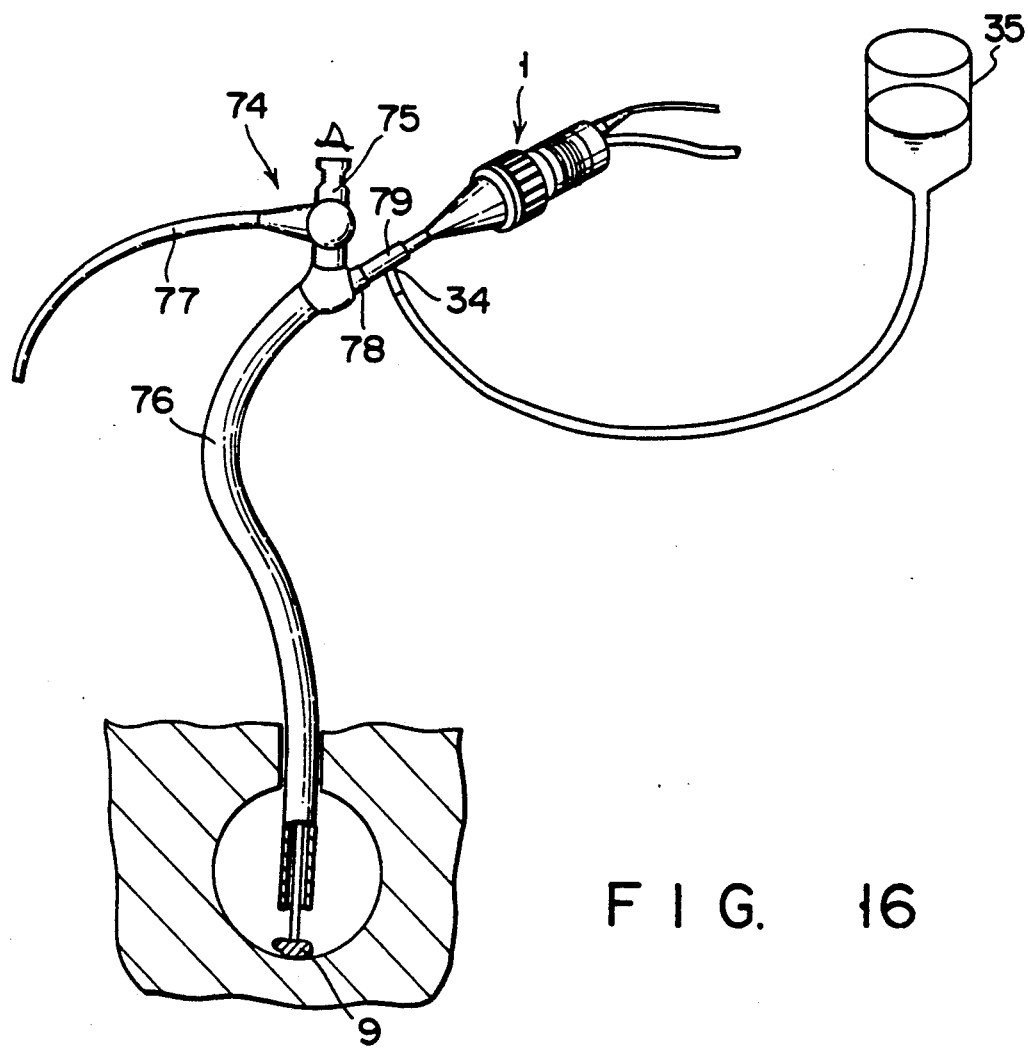
FIG. 16 is a perspective view showing the ultrasonic treatment apparatus of the fifth embodiment combined with an endoscope.

FIGS. 15 and 16 show the fifth embodiment of the present invention. In the fifth embodiment, an ultrasonic treatment apparatus according to the present invention is used in combination with an endoscope.

As shown in FIG. 15, an elastic vibration transmission member 3 is detachably mounted on the distal end of a horn 7 of an ultrasonic probe 1. A small-diameter portion is formed at the distal end portion of a cover 4 of the ultrasonic probe 1. The vibration transmission member 3 is inserted into the small-diameter portion. A seal member 37 is arranged between the vibration transmission member 3 and the small-diameter portion. In addition, as shown in FIG. 15, a coupling adapter 28 incorporating a biasing member 81 is attached to the small-diameter portion of the cover 4. The cover 4 can be slid back and forth with respect to the coupling adapter 28 together with the horn 7 and the vibration transmission member 3.

A sheath 29 is connected to the coupling adapter 28 so that a perfusion liquid can be supplied to substantially the entire vibration transmission member 3 and injected from the tip of the probe 1. A scope attachment 79 which can be attached/detached to/from a channel port 78 of a fiber scope 74 is attached to the distal end of the coupling adapter 28. In addition, a liquid-supply mouthpiece 34 for introducing a perfusion liquid supplied from a liquid-supply bin into the sheath 29 is mounted on the coupling adapter coupled to the sheath 29.

In the ultrasonic treatment apparatus according to the fifth embodiment, therefore, the ultrasonic probe 1 can be attached to the channel port 78 of the fiber scope 74 through the scope attachment 79 so as to be used for a treatment in a body.

A ultrasonic treatment apparatus according to the sixth embodiment of the present invention will be described below with reference to FIGS. 17 and 18.

FIG. 17 shows the overall ultrasonic treatment apparatus of the sixth embodiment, which comprises: piezoelectric elements 5 for generating ultrasonic vibrations upon application of a voltage on electrodes 6 through a power source cord 23 connected to a power source (not shown); an oscillator unit 2 consisting of a horn 7 and a rear metal block 8 which are integrally coupled to each other with a bolt 13 and a nut 14 so as to sandwich the piezoelectric elements 5; a vibration transmission member or probe 3 detachably attached to the distal end of the horn 7 through a first screw-in type coupling portion 82; and a sheath 29 arranged around the outer surface of the probe 3 with a gap defined therebetween. The oscillator unit 2 constitutes a resonance system.

The oscillator unit 2 is fixed by elastically urging a flange 84 formed on the horn 7 against a rear cover 86a through an elastic member 88 such as an O-ring. That is, the elastic member 88 is urged against the flange 84 by using a fixing nut 90 and an elastic member receiving portion 92.

The probe 3 comprises a coupling member 94 having an arcuated portion 3a curving at an angle $\theta$, and a tool 98 detachably connected to the distal end of the coupling member 94 through a second screw-in type coupling portion 96. Note that the coupling portion 94 and the tool 98 may be integrally formed with each other. The inner hole of the probe 3 constitutes a continuous suction path 12 which extends through the oscillator unit 2 and communicates with a suction mouthpiece 19 attached to the proximal end of the rear cover 86a. Emulsified and resected or cut tissues and the like are drawn/removed from the suction path 12 together with a perfusion liquid.

The sheath 29 comprises: a coupling cover 102 which covers the outer surface of the coupling member 94 of the probe 3 with a gap defined therebetween and is detachably connected to a front cover 86b, having a liquid-supply mouthpiece 34, of an ultrasonic probe 1 through a third screw-in type coupling member 100; and a tool cover which is detachably connected to the distal end of the coupling cover 102 through a fourth screw-in type coupling portion 104 and is positioned to cover the outer surface of the tool 98 with a gap defined therebetween and to expose the distal end of the tool 98. The gap between the inner surface of the sheath 29 and the outer surface of the probe 3 is formed as a liquid-supply path 32 for a perfusion liquid supplied from the liquid-supply mouthpiece 34. A perfusion liquid can be supplied to a portion to be operated from the distal end of the sheath 29 through the liquid-supply path 32. In supplying the perfusion liquid, first to third O-rings 108, 110, and 112 serve as seal means for preventing the perfusion liquid from leaking out from the liquid-supply path 32. The first O-ring 108 is arranged between the front cover 86b and the horn 7; the second O-ring 110, near the third screw-in type coupling portion 100 between the front cover 86b and the coupling cover 102; and the third O-ring 112, near the fourth screw-in type coupling portion 104 between the coupling cover 102 and the tool cover 106.

The coupling cover 102 of the sheath 29 consists of a material which can be deformed along the arcuated shape of the arcuated portion 3a of the probe 3, e.g., a resin or rubber material, or a superelastic alloy (a metal, such as lead, which can be deformed). In addition, the outer surface of the coupling cover 102 is made smooth. The coupling cover 102 is preferably transparent and has an elastic force. Although the tool cover 106 may be constituted by either an elastic member or a rigid member, it is preferably transparent. The coupling cover 102 and the tool cover 106 have a continuous smooth surface. In order to prevent the longitudinal axis of the coupling cover 102 from greatly deviating from that or the probe 3 when the coupling cover 102 is bent along the arcuated portion 3a of the probe 3, projections 114 and 116 are formed at two positions of the inner surface of the coupling cover 102 so as to sandwich the arcuated portion 3a. FIG. 18 is a sectional view taken along a line X—X in FIG. 17. Two pairs of projections 114 and 116 are formed on substantially the same plane including the axis of the arcuated portion 3a. However, the number of projections 114 and 116 are not limited to two pairs, but a larger number of projections may be formed. At least a pair of projections 114 and 116 may be respectively formed at two lower positions of the inner surface of the coupling cover 102 with respect to the curving direction of the sheath 29 so as to sandwich the arcuated portion 3a. In addition, projections similar to the projections 114 and 116 may be formed on the inner wall of the tool cover 106 so as to prevent the axis of the tool cover 106 from greatly deviating from that of the tool 98.

A vibration mode of the ultrasonic treatment apparatus having the above-described arrangement according to the sixth embodiment will be described below.

As indicated by the lower portion of FIG. 17, the oscillator unit 2 has a length of a substantially $\frac{1}{2}\lambda$ ($\lambda$: wavelength). The distal end portion of the horn 7 and the proximal end portion of the rear cover 86a respectively correspond to loops of vibrations, and a portion near the flange 84 of the horn 7 corresponds a node of vibrations. The vibrations are transmitted to the probe 3. The probe 3 is then vibrated to transmit the vibrations to the distal end of the tool 98. A tissue, a stone, or a hematoma with which the distal end of the tool 98 is brought into contact is emulsified, cut, resected, or broken. The arcuated portion 3a of the probe 3 corresponds to a loop of vibrations; the portions sandwiching the arcuated portion 3a, nodes of vibrations; and the distal end of the tool 98, a loop of vibrations. Hence, the length of the overall probe 3 is substantially equal to a wavelength $\lambda$. The overall ultrasonic treatment apparatus constitutes a resonance system.

An effective measure to reduce loss of vibrations due to contact of the projections 114 and 116 with the probe 3 is to form the projections 114 and 116 at positions corresponding to portions near nodes of vibrations. In this case, the arcuated portion 3a is located at a loop of vibrations, i.e., at a $\lambda/2$ position from the distal end of the horn 7. However, the position of the arcuated portion 3a is not limited to a loop but may be located at a node of vibrations, i.e., a $\lambda/4$ or $3\lambda/4$ position from the distal end of the horn 7, or may be located at an intermediate portion between a node and a loop, i.e., a $\lambda/8$, $3\lambda/8$, $5\lambda/8$, or $7\lambda/8$ position from the distal end of the horn 7. In addition, the length of the oscillator unit 2 is not limited to $\lambda/2$ as long as it is $n\lambda/2$ (n: integer). The length of the probe 3 is not limited to $\lambda$ as long as it is $n\lambda/2$. In this case, the position of the arcuated portion 3a needs to correspond a loop, a node, or an intermediate portion between a loop and a node of vibrations. The curving angle $\theta$ of the arcuated portion 3a can be arbitrarily selected. In addition, a bent portion may be used in place of the arcuated portion 3a.

In the ultrasonic treatment apparatus according to the sixth embodiment of the present invention, the coupling cover 102 of the sheath 29 which covers the arcuated portion 3a of the probe 3 is designed to be curved along the arcuated portion 3a, and the outer surface of the coupling cover 102 is made smooth. As a result, the sheath 29 has a continuous smooth outer surface, and the outer diameters of the arcuated portion 3a and the portions sandwiching it can be reduced. Therefore, an observation field is less interfered, and a safe, reliable treatment can be performed for a deep portion in a living body. In addition, the coupling cover 102 is curved along the arcuated portion 3a. Therefore, when the coupling cover 102 is curved, it is pulled in its axial direction to expand in the axial direction and contract in the radial direction. As a result, the outer diameter of the coupling cover 102 is reduced.

Since the coupling cover 102 is deformed along an arcuated shape with respect to an arbitrary curving angle $\theta$, one sheath can be applied to probes having various curving angels $\theta$. Therefore, versatility of the sheath 29 can be improved and becomes more economical. Moreover, the sheath 29 can be applied to a bent probe or a straight probe without an arcuated or bent portion.

Since the sheath 29 has a continuous smooth outer surface, there is no danger of damaging tissues with the sheath 29. In addition, since blood and the like do not easily adhere to the outer surface of the sheath 29, its cleaning is facilitated. Moreover, since the projections 114 and 116 are formed on the inner surface of the sheath 29, the axis of the sheath 29 does not deviate from that of the probe 3. That is, the liquid-supply path 32 can be ensured, and a perfusion liquid can be reliably poured.

FIG. 19 shows the first modification of the sheath.

In this modification, a large number of projections 118 are radially formed on the inner surface of the coupling cover 102.

FIG. 20 shows the second modification of the sheath.

An ultrasonic treatment apparatus according to the second modification comprises the sheath 29 obtained by integrally forming the coupling cover 102 and the tool cover 106 in the sixth embodiment, and the probe 3 obtained by integrally forming the coupling member 94 and the tool 28. A material which can be deformed is used for the entire sheath 29 or at least portions sandwiching an arcuated portion 29a. The projections 114 are formed at positions of the inner surface of the sheath 29 which are located near the distal end and correspond to a node of vibrations.

In the ultrasonic treatment apparatus according to the second modification, the sheath 29 is integrally formed and so is the probe 3. Therefore, the number of parts can be decreased, and the apparatus becomes more economical. Since the second and the fourth screw-in type coupling portions 96 and 104 are not used, a reliable liquid-tight seal and high durability can be obtained. In addition, assembly of the probe 3 and the sheath 29 during a surgical operation is facilitated, and hence the operation can be quickly performed.

FIG. 21 shows the third modification of the sheath.

In the third modification, a fit-in type coupling portion 124 is employed in place of the screw-in type coupling portion for the front cover 86b and the coupling cover 102 in the sixth embodiment. More specifically, one rib 126 is arranged at the distal end of a front cover 86b, and the other rib 128 is arranged at the proximal end of the coupling cover 102 so as to ride on and elastically engage with one rib 126. When the coupling cover 102 is pushed into the front cover 86b, the ribs 126 and 128 are engaged with each other with a click. The ribs 126 and 128 can be separated from each other by pulling them. Note that the same structure may be applied to a coupling portion for the coupling cover 102 and a tool cover 106. In addition, the other rib 128 on the coupling cover 102 side may be omitted, and the proximal end portion of the coupling cover 102 may be forcibly expanded and covered on one rib 126 of the front cover 86b.

In an ultrasonic treatment apparatus according to the third modification, attachment/detachment of the sheath 29 and the front cover 86b, or the coupling cover 102 of the sheath 29 and the tool cover 106 can be performed with a simple operation, and hence is facilitated. In addition, the sheath 29 is rotatable with respect to the front cover 86; and the tool cover, with respect to the coupling cover 102. Therefore, even if a rotational force is applied from the tissue of a portion to be treated to the sheath 29 or the tool cover 106, this force can be canceled by the rotation of the fit-in type coupling portion 124. Hence, damage on the tissue can be prevented, and a safe surgical operation can be performed. In addition, detachment of the sheath 29 or the tool cover 106 due to loosening of the fit-in type coupling portion 124 during an operation can be prevented.

The projections 112 and 116 need not be formed at two positions to sandwich an arcuated or bent portion but may be formed at three or more positions in the longitudinal direction of the coupling cover, or may be continuously formed.

The seventh embodiment of the present invention will be described below with reference to FIGS. 22 and 23.

Figure 22:
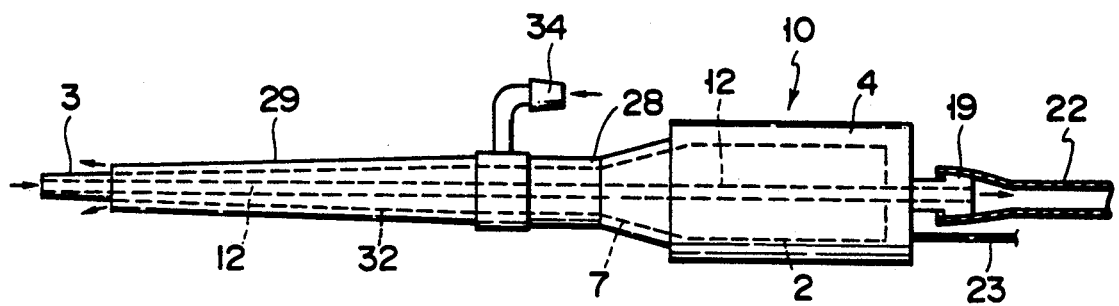
FIG. 22 is a side view of an ultrasonic treatment apparatus according to the seventh embodiment of the present invention.

FIG. 22 shows an overall arrangement of an ultrasonic treatment apparatus according to the seventh embodiment. Reference numeral 10 denotes a grip portion having a cover 4. An ultrasonic oscillator unit (ultrasonic vibration generating section) 2 is arranged in the grip portion 10. A vibration transmission member, that is, a probe 3 is connected to the ultrasonic oscillator unit 2 through a horn 7. Ultrasonic vibrations generated by the ultrasonic oscillator unit 2 are increased in amplitude by the horn 7 and are transmitted to the probe 3.

The probe 3 is covered with a cylindrical sheath 29. The sheath 29 has a proximal end portion connected to a cover 4 through a connecting member 28 and is arranged concentrically with the probe 3 so as not to be in contact with its outer surface. A portion near the distal end work portion of the probe 3 is exposed from the distal end of the sheath 29.

Figure 23:
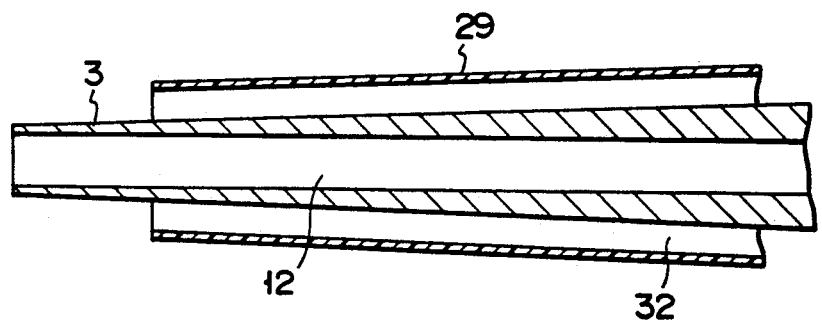
FIG. 23 is a longitudinal sectional view showing a distal end portion of the ultrasonic treatment apparatus in FIG. 22.

As shown in FIG. 23, a gap between the probe 3 and the sheath 29 constitutes a flow path 32 through which a fluid such as sterile water or a physiological saline solution supplied from a liquid-supply mouthpiece 34 flows. The flow path 32 communicates with the liquid-supply mouthpiece 34 coupled to the connecting member 28, so that sterile water or a physiological saline liquid is supplied to the flow path 32 through a liquid-supply tube connected to the liquid-supply mouthpiece 34.

As shown in FIG. 23, the probe 3 consists of a metal hollow pipe, and its inner surface defines a suction path 12. The distal end portion of the outer surface of the probe 3 is tapered. The probe 3 is detachably coupled to the distal end of the horn 7. Probes different from the probe 3 can be selectively coupled to the distal end of the horn 7.

The suction path 12 of the probe 3 communicates with a suction mouthpiece 19 through an inner hole extending through the horn 7 and the ultrasonic oscillator unit 2. A suction tube 22 is connected to the suction mouthpiece 19 so that a suction pump can perform a suction operation through the suction tube 22.

As shown in FIG. 23, the sheath 29 which covers the probe 3 consists of a flexible resin material and is formed into a tapered shape having a uniform, small thickness. For example, a thin, flexible fluoroplastic material is suitably used as the flexible resin material.

The ultrasonic treatment apparatus according to the seventh embodiment is used in the following procedures. The probe 3 is introduced, together with the sheath 29, into a body cavity in which a portion to be treated is present. A fluid such as sterile water or a physiological saline solution is supplied from the liquid-supply mouthpiece 34 into the flow path 32 constituted by the gap between the probe 3 and the sheath 29, and is caused to flow out from the distal end opening of the sheath 29 into the cavity through the flow path 32. With this operation, the probe 3 is cooled and a portion around the portion to be treated is cleaned. Meanwhile, the liquid in the cavity, which was used for cleaning, is drawn and discharged outside by the suction pump through the suction path 12 in the probe 3, the suction mouthpiece 19, and the suction tube 22.

During this operation, ultrasonic vibrations generated by the ultrasonic oscillator unit 2 are increased in amplitude and are transmitted to the distal end work portion of the probe 3 through the probe 3. The distal end of the probe 3 is brought into contact with the morbid portion to break or emulsify its tissue. The broken or emulsified tissue is discharged outside, together with the fluid for cleaning, through the suction path 12 in the probe 3, the suction mouthpiece 19, and the suction tube 22. Note that reference numeral 23 denotes a driving power source cord extending to the ultrasonic oscillator unit 2.

The sheath 29 covering the probe 3 consists of a flexible resin material and is formed into a tapered shape having a uniform, small thickness. The sheath 29 can be manufactured by molding a fluoroplastic tube into a tapered shape. Hence, a process for forming the sheath 29 is facilitated, and the manufacturing cost can be reduced. In practice, the sheath 29 has a thickness of about 0.2 to 0.4 mm. Since formation of such a thin sheath is relatively easy, the sheath 29 can be thinned throughout its entire length. Therefore, observation of the portion to be treated is less interfered with the sheath 29 during an operation using the ultrasonic treatment apparatus. In addition, since the sheath 29 is flexible, positioning of the centers of the probe 3 and the sheath 29 in assembling the ultrasonic treatment apparatus can be easily performed. Moreover, since the sheath 29 consists of a fluoroplastic material, it is resistant to 200° C. or more. Therefore, even if the prove 3 generates heat during ultrasonic vibration, the sheath 29 is free from deformation or damage during the operation, thus performing a safe operation.

Figure 24:
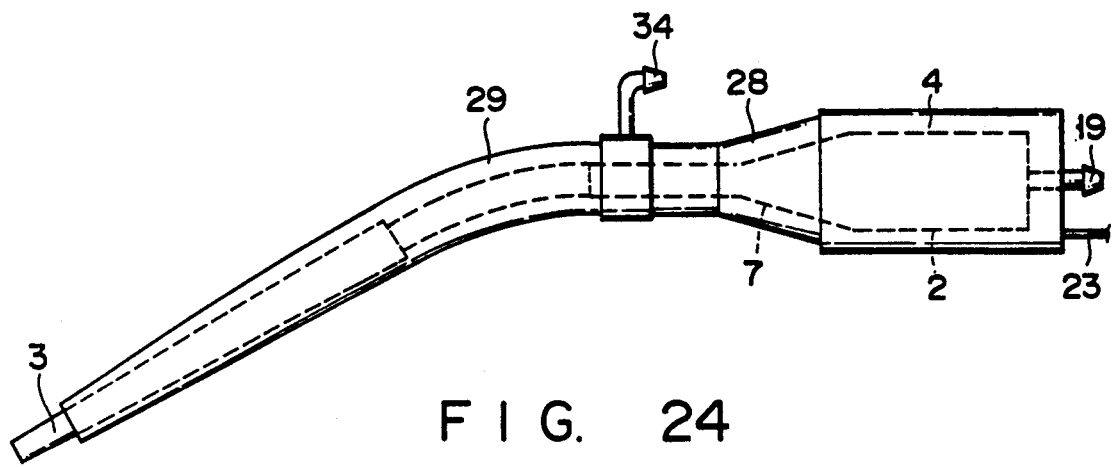
FIG. 24 is a side view showing the first modification of a vibration transmission member according the seventh embodiment.

FIG. 24 shows the first modification of the ultrasonic treatment apparatus according to the seventh embodiment of the present invention. In the first modification, an arcuated probe 3 is used. A flexible fluoroplastic sheath 29 which is integrally formed throughout its entire length covers the arcuated probe 3 together with its arcuated portion.

Figure 25:
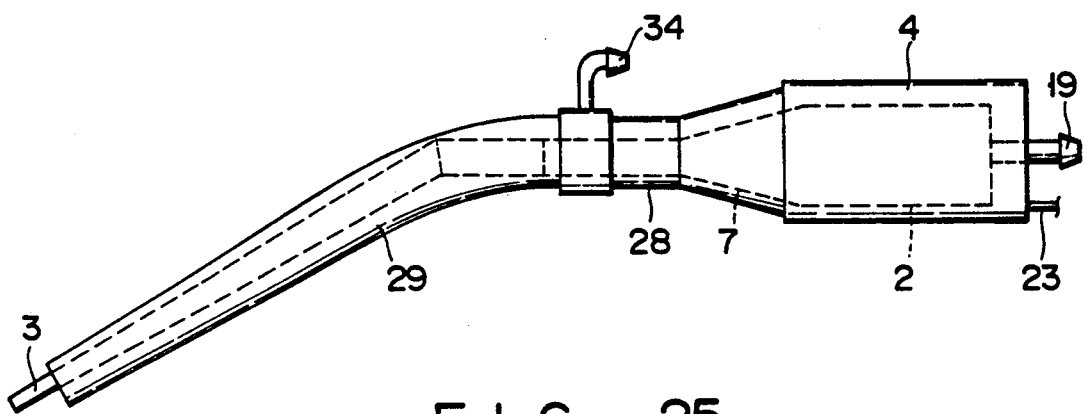
FIG. 25 is a side view showing the second modification of the vibration transmission member.

FIG. 25 shows the second modification of the seventh embodiment. In the second modification, a bent probe 3 is used. A flexible fluoroplastic sheath 29 which is integrally formed throughout covers the bent probe 3 together with its bent portion.

Note that the sheath 29 may be made of a transparent material (e.g., a fluoroplastic). In this case, even if the distal end portion of the probe is placed behind the sheath, the distal end of the probe can be seen. As a result, operability is improved. In place of a fluoroplastic, a silicone resin, nylon, or the like may be used as a material for the sheath.

Figure 26:
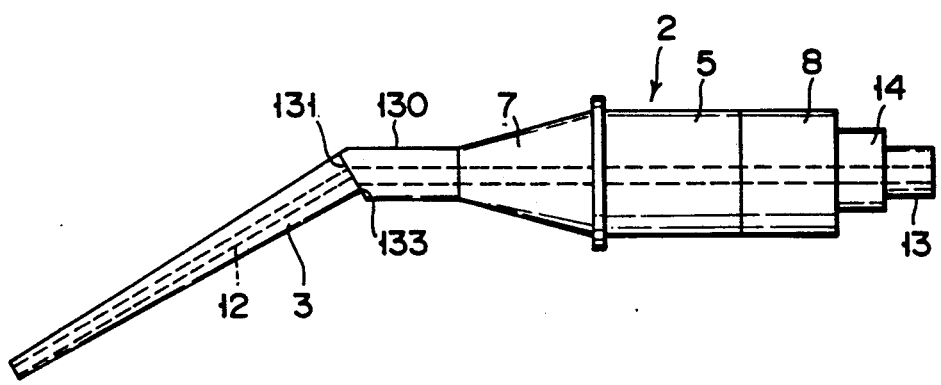
FIG. 26 is a side view of an ultrasonic treatment apparatus according to the eighth embodiment of the present invention.

The eighth embodiment of the present invention will be described below. FIGS. 26 and 27 show an ultrasonic treatment apparatus according to the eighth embodiment. This treatment apparatus includes a horn 7 having a cylindrical distal end portion 130. An end face 131 of the portion 130 is inclined downward. A proximal end face 133 of a probe 3 is joined to the end face 131 by threadable engagement. In the treatment apparatus including the probe 3 having such a bent connecting portion, the end face 131 is matched with the circular shape of the proximal end face 133 of the probe 3 by cutting a horn-like edge portion 132 protruding from the end face 131 of the cylindrical distal end portion 130 of the horn 7. That is, the distal end face 131 of the portion 130 of the horn 7 and the proximal end face 133 abutting thereon are formed into substantially the same circular shape. In addition, in the eighth embodiment, especially the upper edge of the end face 131 of the cylindrical distal end portion 130 of the horn 7 almost perfectly coincides with the upper edge of the proximal end face 133 of the probe 3 abutting the end face 131. With this arrangement, the probe 3 is coupled to the horn 7 so as to be inclined with respect to its central axis, while the outer surfaces of the bent connecting portion, which are located on the external angle side of the inclined angle of the connecting portion, are coupled to each other without a step.

Since the edge portion 132 protruding in the form a horn on the upper surface side of the probe 3 is cut from the connecting portion constituting the bent portion of the probe 3, an operator can see the distal end portion of the probe 3 without interference with his field of view and can perform a safe surgical treatment.

FIGS. 29 and 30 show a modification of the probe connecting structure of the eighth embodiment. In this modification, the upper surface portion of a cylindrical distal end portion 130 of a horn 7 is cut obliquely. That is, an upper portion of an elliptic end face 131 is cut. In addition, an end face 133 of the probe 3 is welded to the end face 131 of the cylindrical distal end portion 130 of the horn.

A cut upper surface 134 of the cylindrical distal end portion 130 of the horn 7 is designed to be parallel to the central axis of the probe 3 and to be at the same level as that of the upper surface of the probe 3.

Similarly, in this arrangement, since an edge portion 132 protruding in the form of a horn on the upper side of the probe 3 is cut off from the connecting portion constituting the bent portion of the probe 3, an operator can see the distal end portion of the probe 3 without interference with his field of view and can perform a safe surgical operation.

If the wavelength of ultrasonic vibrations to be transmitted to the probe 3 is set to be $\lambda$, one or more intermediate vibration transmission members (not shown) corresponding to a length of an integer multiple of $\lambda/2$ may be inserted between the horn 7 and the probe 3 which bends and extends therefrom. A connecting portion between the intermediate transmission member and the probe 3 may have the same structure as that of the connecting portion in the eighth embodiment or the modification.

With the intermediate vibration transmission member, the probe distal end of the ultrasonic treatment apparatus can more easily reach a deep portion in a living body.

FIGS. 30 and 31 show an ultrasonic treatment apparatus according to the ninth embodiment of the present invention. A probe 3 of the ninth embodiment includes a bent portion 3a and is constituted by a coupling member 94 detachably coupled to the bent distal end of the coupling member 94 through a second coupling portion 96. Vibrations generated by a vibration generating section including an ultrasonic oscillator are transmitted to the tool 98 through the horn 7. The first and second connecting portions 84 and 96 are constituted by threads. The coupling member 94 and the tool 98 are tapered toward their distal ends so that vibrations transmitted from the horn 7 are increasingly amplified toward the distal end of the probe 3.

Note that the tool 98 may be directly coupled to the horn 7 without the coupling member 94.

As shown in FIG. 30, the probe 3 is covered with a coupling adapter 28 coupled by a front cover for covering the horn 7 and by a third coupling portion 100, a sheath 29 for surrounding part of the tool 98 and the coupling member 94 with a gap defined therebetween, and a clamp member 138 for clamping and fixing the sheath 29. An O-ring 110 for sealing is inserted in the gap between the third coupling portion 100 and the coupling adapter 28. The sheath 29 is made of a flexible material and has a flange portion 136 at its proximal end portion. The sheath 29 can be liquid-tightly fixed to the coupling adapter 28 by clamping and fixing it between the clamp member 138 and the coupling adapter 28.

In the ninth embodiment, since the sheath 29 is made of a flexible material as described above, when the sheath 29 is attached to the probe 3, the bent portion 3a of the probe 3 can be smoothly passed therethrough.

Note that the entire sheath 29 need not be made of the same flexible material and the flexibility of the sheath 29 may be partially changed. For example, a fluoroplastic or a silicone resin is preferably used as a material of the sheath 29. However, the present invention is not limited to these materials.

FIG. 31 shows a modification of the above-described sheath. In this modification, a bellows portion 29b is formed on a bent portion 29a of the sheath 29. With this bellows portion 29b, the sheath 29 can be easily bent along a bent portion 3a of a probe 3.

What is claimed is:
1. An ultrasonic treatment apparatus comprising:
   an ultraxonic probe having:
      ultrasonic vibration generating means for generating ultrasonic vibrations;
      vibration transmission means for transmitting generated vibrations, said vibration transmission means including a vibration transmission member detachably coupled to said generating means, said vibration transmission member having an outer peripheral surface; and
      a distal end;
   a sheath covering at least the outer peripheral surface of said vibration transmission member of said ultrasonic probe, said sheath being attachable to and detachable from said vibration transmission member, said sheath having a fluid supply attaching portion, and said sheath at least partly defining a fluid flow path between said sheath and said vibration transmission member;
   fluid supply means, attached to said fluid supply attaching portion of said sheath, for supplying a fluid into said fluid flow path defined between said vibration transmission member and said sheath; and
   seal means mounted on said sheath at a location nearer to said vibration generating means than said fluid supply attaching portion of said sheath, for preventing the fluid from flowing to said vibration generating means, said seal means cooperating with a portion of said vibration transmission member which corresponds to a node of vibration, and said portion of said vibration transmission member with which said seal means cooperates having a diameter which is not stepped but gradually decreases toward the distal end of the probe so as to form a tapered portion of said vibration transmission member, such that said seal means is arranged between said tapered portion of said vibration transmission member and said sheath covering an outer peripheral surface of said tapered portion;

and a given portion of each of said vibration transmission member and said sheath being detachably attached to the vibration generating means at respective connecting portions thereof, and wherein the connecting portions of said vibration transmission member and sheath are located in close proximity to each other, wherein said seal means and sheath are removable together when removed from the apparatus.

2. The apparatus according to claim 1, further comprising control means for driving and controlling said ultrasonic probe.

3. The apparatus according to claim 1, further comprising:

first suction path means formed in said ultrasonic probe;

second suction path means, which communicates with said first suction path means and a location outside of said ultrasonic probe, for passing an object to be treated which is broken by said ultrasonic probe through the second suction path means;

vessel means, arranged substantially midway along said second suction path means, for storing the drawn object; and suction means for evacuating said vessel means to a negative pressure, said suction means including a pump.

4. The apparatus according to claim 3, further comprising detecting means for detecting an excess negative pressure in said vessel means when said first and/or second suction path means between said suction means and a tip of said probe clogs up.

5. The apparatus according to claim 4, further comprising means for generating an alarm when said detecting means detects the excess negative pressure.

6. The apparatus according to claim 4, further comprising means for stopping said pump when said detecting means detects the excess negative pressure.

7. The apparatus according to claim 4, wherein said pump has suction and discharge ports, the apparatus further comprising:

means for switching paths respectively communicating with the suction and discharge ports of said pump when said detecting means detects the excess negative pressure, and thereafter, when the operation of said pump is started, said switching means switches the paths which communicate with said suction port and discharge port of said pump.

* * * * *